US008163483B2

(12) United States Patent
Pulst

(10) Patent No.: US 8,163,483 B2
(45) Date of Patent: *Apr. 24, 2012

(54) COMPOSITIONS AND METHODS FOR SPINOCEREBELLAR ATAXIA

(75) Inventor: Stefan M. Pulst, Salt Lake City, UT (US)

(73) Assignee: Cedars-Sinai Medical Center, Los Angeles, CA (US)

(*) Notice: Subject to any disclaimer, the term of this patent is extended or adjusted under 35 U.S.C. 154(b) by 102 days.

This patent is subject to a terminal disclaimer.

(21) Appl. No.: 12/386,427

(22) Filed: Apr. 17, 2009

(65) Prior Publication Data

US 2009/0286243 A1    Nov. 19, 2009

Related U.S. Application Data

(63) Continuation-in-part of application No. 11/411,233, filed on Apr. 24, 2006.

(60) Provisional application No. 60/720,915, filed on Sep. 26, 2005, provisional application No. 60/674,182, filed on Apr. 22, 2005.

(51) Int. Cl.
*C07H 21/04*     (2006.01)
*C12Q 1/68*      (2006.01)

(52) U.S. Cl. ...... 435/6.1; 435/6.11; 435/6.12; 435/91.1; 435/91.2; 536/23.1; 536/24.3

(58) Field of Classification Search .......................... None
See application file for complete search history.

(56) References Cited

U.S. PATENT DOCUMENTS 7,585,629 B2 * 9/2009 Pulst ............................. 435/6.16
2003/0092019 A1   5/2003 Meyer et al.

FOREIGN PATENT DOCUMENTS

WO    WO 2006/116407 A2    11/2006

OTHER PUBLICATIONS

Waters et al. (Annals of Neurology, vol. 58, No. 6, Poster Session, Dec. 2005).*
Waters et al. (Nature Genetics, vol. 38, No. 4, pp. 447-451, Feb. 26, 2006).*
Figueroa et al. (Neurology, vol. 68, Suppl 1, IN2-2.008, Mar. 20, 2007.*
Waters et al. (Cerebellum, vol. 7, pp. 165-169, Jul. 1, 2008).*
Figueroa, et al., "KCNC3: Phenotype, Mutations, Channel Biophysics—a Study of 260 Familial Ataxia Patients," *Hum Mutat.*, 31(2): 191, 14 pages, Feb. 2010.
Figueroa, K.P., et al., Frequency of KCNC3 DNA Variants as Causes of Spinocerebellar Ataxia 13 (SCA13), PLoS ONE 6(3): e17811, doi:10.1371/journal.pone.0017811 (Mar. 2011).
Figueroa, K.P., et al., "SCA13: KCNC3 Mutations and Genotype/ Phenotype Correlations in 260 Familial Ataxia Patients," *Neurology*, 68(Supp 1):A82 (Mar. 2007) (Abstract Only).

Brusco, A., et al., "Molecular Genetics of Hereditary Spinocerebellar Ataxia: Mutation Analysis of Spinocerebellar Ataxia Genes and CAG/CTG Repeat Expansion Detection in 225 Italian Families," *Arch. Neurol.*, 61: 727-733 (May 2004).
Kalman, K., et al., "Genomic Organization, Chromosomal Localization, Tissue Distribution, and Biophysical Characterization of a Novel Mammalian *Shaker*-related Voltage-gated Potassium Channel, Kv1.7*," *The Journal of Biological Chemistry*, 273(10): 5851-5857 (Mar. 6, 1998).
Wang, D., et al., "NADPH-oxidase and hydrogen peroxide-sensitive K+ channel may function as an oxygen sensor complex in airway chemoreceptors and small cell lung carcinoma cell lines," *Proc. Natl. Acad. Sci. USA* (*Medical Sciences*), 93: 13182-13187 (Nov. 1996).
Aggarwal, S.K. and MacKinon, R., "Contribution of the S4 Segment to Gating Charge in the *Shaker* K+ Channel," *Neuron* 16:1169-1177 (1996).
Broman, K.W., et al., "Comprehensive Human Genetic Maps: Individual and Sex-Specific Variation in Recombination," *Am. J. Hum. Genet.* 63(3):861-869 (1998).
Chen, D.H., et al., "The Clinical and Genetic Spectrum of Spinocerebellar Ataxia 14," *Neurology* 64:1258-1260 (2005).
Covarrubias, M., et al., "*Shaker, Shal, Shah, and Shaw* Express Independent K+ Current Systems," *Neuron* 7:763-773 (1991).
Delwart, E.L. et al., "Genetic Relationships Determined by a DNA Heteroduplex Mobility Assay: Analysis of HIV-1 *Env* Genes," *Science* 262:1257-1261 (1993).
Dib, C. et al., "A Comprehensive Genetic Map of the Human Genome Based on 5,264 Microsatellites," *Nature* 380:152-154 (1996).
Dudding, T.E. et al., "Autosomal Dominant Congenital Non-Progressive Ataxia Overlaps SCA15 Locus," *Neurology* 63:2288-2292 (2004).
Duprat, F., "Susceptibility of Cloned K+ Channels to Reactive Oxygen Species," *Proc. Natl. Acad. Sci. U.S.A.* 92:11796-11800 (1995).
Dworakowska, B. and Dolowy, K., "Ion Channels-Related Diseases," *Acta Bioch. Pol.* 47:685-703 (2000).
Espinosa, F. et al., "Alcohol Hypersensitivity, Increased Locomotion, and Spontaneous Myoclonus in Mice Lacking the Potassium Channels Kv3.1 and Kv3.3," *J. Neurosci.* 21(17):6657-6665 (2001).
Ghanshani, P. et al., "Genomic Organization, Nucleotide Sequence, and Cellular Distribution of a *Shaw*-Related Potassium Channel Gene, Kv3.3, and Mapping of Kv3.3 and Kv3.4 to Human Chromosomes 19 and 1," *Genomics* 12(2):190-196 (1992).
Goldman-Wohl, D.S. et al., "Kv3.3b: A Novel *Shaw* Type Potassium Channel Expressed in Terminally Differentiated Cerebellar Purkinje Cells and Deep Cerebellar Nuclei," *J. Neurosci.* 14(2):511-522 (1994).
Gomez, C.M. and Subramony, S.H., "Dominantly Inherited Ataxias," *Semin. Pediatr. Neurol.* 10(3): 210-222 (2003).
Graves, T.D. and Hanna, M.G., "Neurological Channelopathies," *Postgrad. Med. J.* 81:20-32 (2005).
Hayashi, S.I. et al., "PCR Detection of an A/G Polymorphism within Exon 7 of the CYP1A1 Gene," *Nucleic Acids Research* 19(17):4797 (1991).
Herman-Bert, A. et al., "Mapping of Spinocerebellar Ataxia 13 to Chromosome 19q13.3-q13.4 in a Family with Autosomal Dominant Cerebellar Ataxia and Mental Retardation," *Am. J. Hum. Genet.* 67:229-235 (2000).

(Continued)

*Primary Examiner* — Jeanine A Goldberg
(74) *Attorney, Agent, or Firm* — Hamilton, Brook, Smith & Reynolds, P.C.

(57) ABSTRACT

Mutations in the KCNC3 (Kv3.3) voltage-gated potassium channel gene result in spinocerebellar ataxia.

10 Claims, 12 Drawing Sheets

OTHER PUBLICATIONS

Kruglyak, L. et al., "Parametric and Nonparametric Linkage Analysis: A Unified Multipoint Approach," *Am. J. Hum. Genet.* 58:1347-1363 (1996).

Kruglyak, L. and Lander, E.S., "Faster Multipoint Linkage Analysis Using Fourier Transforms," *J. Comput. Biol.* 5(1):1-7 (1998).

Lieberman, A.P. and Fischbeck, K.M., "Triplet Repeat Expansion in Neuromuscular Disease," *Muscle Nerve* 23:843-850 (2000).

Long, S.B. et al., "Crystal Structure of a Mammalian Voltage-Dependent *Shaker* Family $K^+$ Channel," *Science* 309:897-903 (2005).

Mantuano, E. et al., "Spinocerebellar Ataxia Type 6 and Episodic Ataxia Type 2: Differences and Similarities Between Two Allelic Disorders," *Cytogenet Genome Res* 100(1-4):147-153 (2003).

Martina, M. et al., "Properties and Functional Role of Voltage-Dependent Potassium Channels in Dendrites of Rat Cerebellar Purkinje Neurons," *J. Neurosci.* 23(13):5698-5707 (2003).

Matsuura, T. et al., "Large Expansion of the ATTCT Pentanucleotide Repeat in Spinocerebellar Ataxia Type 10," *Nat. Genet* 26: 191-194 (2000).

McKay, B.E. and Turner, R.W., "Kv3 $K^+$ Channels Enable Burst Output in Rat Cerebellar Purkinje Cells," *Eur. J. Neurosci.* 20:729-739 (2004).

McKay, B.E. and Turner, R.W., "Physiological and Morphological Development of the Rat Cerebellar Purkinje Cell," *J. Physiol.* 567.3:829-850 (2005).

Michalik, A. and Van Broeckhoven C., "Pathogenesis of Polyglutamine Disorders: Aggregation Revisited," *Hum. Mol. Genet.* 12(2):R173-R186 (2003).

Mulley, J.C. et al., "Channelopathies as a Genetic Cause of Epilepsy," *Curr. Opin. Neurol.* 16:171-176 (2003).

Mullis, K.B. et al. (Eds.), "The Polymerase Chain Reaction," Birkhauser: Boston (1994).

Pulst, S.M. (Ed.), "Genetics of Movement Disorders," Academic Press: San Diego (2003).

Pulst, S.M., "Neurogenetics: Single Gene Disorders," *J. Neurol. Neurosurg. Psych.* 74:1608-1614 (2003).

Rae, J.L. and Shepard, A.R., "Kv3.3 Potassium Channels in Lens Epithelium and Corneal Endothelium," *Exp. Eye. Res.* 70:339-348 (2000).

Ranum, L.P. and Day, J.W., "Myotonic Dystrophy: RNA Pathogenesis Comes Into Focus," *Am. J. Hum. Genet.* 74:793-804 (2004).

Raskind, W.H. et al., "Familial Spastic Paraparesis: Evaluation of Locus Heterogeneity, Anticipation, and Haplotype Mapping of the SPG4 Locus on the Short Arm of Chromosome 2," *Am. J. Med. Genet.* 74(1):26-36 (1997).

Rudy, B. and McBain, C.J., "Kv3 Channels: Voltage-Gated K+ Channels Designed for High-Frequency Repetitive Firing," *Trends Neurosci.* 24(9):517-526 (2001).

Ruppersberg, J.P. et al., "Regulation of Fast Inactivation of Cloned Mammalian $I_K(A)$ Channels by Cysteine Oxidation," *Nature* 352:711-714 (1991).

Schöls, L. et al., "Autosomal Dominant Cerebellar Ataxias: Clinical Features, Genetics, and Pathogenesis," *Lancet Neurol.* 3:291-304 (2004).

Schulteis, C.T. et al., "Subunit Folding and Assembly Steps are Interspersed during Shaker Potassium Channel Biogenesis," *J. Biol. Chem.* 273(40):26210-26217 (1998).

Seoh, S.A, et al., "Voltage-Sensing Residues in the S2 and S4 Segments of the Shaker K+ Channel," *Neuron* 16:1159-1167 (1996).

Sheffield, V.C. et al., "Identifying DNA Polymorphisms by Denaturing Gradient Gel Electrophoresis," in *PCR Protocols: A Guide to Methods and* Applications, Innis, M.A. et al., (Eds.), pp. 206-218 (1990).

Shen, N.V. and Pfaffinger, P.J., "Molecular Recognition and Assembly Sequences Involved in the Subfamily-Specific Assembly of Voltage-Gated K+ Channel Subunit Proteins," *Neuron* 14:625-633 (1995).

Shieh, C.C. et al., "Role of Transmembrane Segment S5 on Gating of Voltage-Dependent $K^+$ Channels," *J. Gen. Physiol.* 109:767-778 (1997).

Silverman, W.R. et al., "$Mg^{2+}$ Modulates Voltage-Dependent Activation in Either-à-go-go Potassium Channels by Binding Between Transmembrane Segments S2 and S3," *J. Gen. Physiol.* 116:663-677 (2000).

Smith-Maxwell, C.J. et al., "Uncharged S4 Residues and Cooperativity in Voltage-Dependent Potassium Channel Activation," *J. Gen. Physiol.* 111:421-439 (1998).

Stevanin, G. et al., "Mutation in the Catalytic Domain of Protein Kinase C γ and Extension of the Phenotype Associated with Spinocerebellar Ataxia Type 14," *Arch. Neurol.* 61:1242-1248 (2004).

Trottier, Y, et al., "Polyglutamine Expansion as a Pathological Epitope in Huntington's Disease and Four Dominant Cerebellar Ataxias," *Nature* 378:403-406 (1995).

Vega-Saenz de Miera, E. and Rudy, B., "Modulation of $K^+$ Channels by Hydrogen Peroxide," *Biochem Biophys Res Comm* 186(3):1681-1687 (1992).

Waters, M.F. et al., "An Autosomal Dominant Ataxia Maps to 19q13: Allelic Heterogeneity of SCA13 or Novel Locus?," *Neurology* 65:1111-1113 (epub 2005).

Weiser, M. et al., "Differential Expression of *Shaw*-related $K^+$ Channels in the Rat Central Nervous System," *J. Neurosci.* 14(3):949-972 (1994).

White, M.B. et al., "Detecting 3Single Base Substitutions as Heteroduplex Polymorphisms," *Genomics* 12:301-306 (1992).

Winter, E. et al,, "A Method to Detect and Characterize Point Mutations in Transcribed Genes: Amplification and Overexpression of the Mutant c-Ki-*ras* Allele in Human Tumor Cells," *Proc. Natl. Acad. Sci.* 82:7575-7579 (1985).

Zander, C. et al., "Multivariate Analysis of Factors influencing Repeat Expansion Detection," *Genome Res* 8:1085-1094 (1998).

Zu, L. et al., "Mapping of a New Autosomal Dominant Spinocerebellar Ataxia to Chromosome 22," *Am. J. Hum. Genet.* 64:591-599 (1999).

Waters, M.F., et al., "Mutations in Voltage-Gated Potassium Channel KCNC3 Cause Degenerative and Developmental Central Nervous System Phenotypes," *Nature Genetics*, 38(4): 447-451 (Apr. 2006).

Browne, D.L. et al., "Episodic Ataxia/Myokymia Syndrome is Associated with Point Mutations in the Human Potassium Channel Gene, *KCNA1*," Nature Genetics 8:136-140 (1994).

Dror, V. et al., "hKCa3/KCNN3 Potassium Channel Gene: Association of Longer CAG Repeats with Schizophrenia in Israeli Ashkenazi Jews, Expression in Human Tissues and Localization to Chromosome 1g21," *Mol. Psychiatry* 4:254-260 (1999).

Guy, C.A. et al., "No Association Between a Polymorphic CAG Repeat in the Human Potassium Channel Gene hKCa3 and Bipolar Disorder," *Am. J. of Medical Genetics* 88:57-60 (1999).

Hirschhorn, J.N. et al., "A Comprehensive Review of Genetic Association Studies," *Genet. Med.* 4(2):45-61 (2002).

Ioannidis, J.P.A. et al., "Replication Validity of Genetic Association Studies," Nature Genetics 29:306-309 (2001).

Laurent, C. et al., "CAG Repeat Polymorphisms in KCNN3 (HSKCa3) and PPP2R2B Show No Association or Linkage to Schizophrenia," *Am. J. of Medical Genetics* 11613:45-50 (2003).

Notification of Transmittal of the International Search Report and the Written Opinion of the International Searching Authority, or the Declaration, International Search Report, and Written Opinion, International Application No. PCT/US2006/015640, Mailed on Apr. 24, 2008.

Notification Concerning Transmittal of International Preliminary Report on Patentability, and International Preliminary Report on Patentability, International Application No. PCT/US2006/015640, Mailed on Mar. 19, 2009.

Office Action, U.S. Appl. No. 11/411,233, Mail Date Mar. 27, 2008.
Office Action, U.S. Appl. No. 11/411,233, Mail Date Nov. 24, 2008.
Advisory Action, U.S. Appl. No. 11/411,233, Mail Date Mar. 9, 2009.
Notice of Allowance, U.S. Appl. No. 11/411,233, Mail Date Jun. 19, 2009.

\* cited by examiner

| Individual | I-1 | II-1 | II-4 | II-5 | II-6 | II-7 | II-10 | II-14 | III-2 | III-3 |
|---|---|---|---|---|---|---|---|---|---|---|
| Gait ataxia | +++ | +++ | ++ | ++ | + | + | + | + | + | + |
| Limb ataxia | +++ | +++ | | + | + | | | + | + | + |
| Titubation | ++ | | | + | | | | | | |
| Hypotonia | ++ | ++ | | | | | | + | ++ | |
| Dysarthria | ++ | ++ | | + | | | | + | + | + |
| Nystagmus | | | | + | | | | | | |
| Hyperreflexia | | | | ++ | | | | + | | |

FIG. 3

| Species (common name) | Seq. ID No. | S4Domain | Seq. ID No. | S5Domain |
|---|---|---|---|---|
| Homosapiens (human) | SEQ ID NO: 20 | FLRVVRFVRILRIFKL TRHFVGL | SEQ ID NO: 21 | FLLIIFLALGVL IFATMIYYA |
| Tetraodon nigroviridis (pufferfish) | SEQ ID NO: 24 | FLRVVRFVRILRIFKL TRHFVGL | SEQ ID NO: 25 | FLLIIFLALGVL IFATMIYYA |
| Fugu rubripes (pufferfish) | SEQ ID NO: 26 | FLRVVRFVRILRIFKL TRHFVGL | SEQ ID NO: 27 | FLLIIFLALGVL IFATMIYYA |
| Mus musculus (mouse) | SEQ ID NO: 28 | FLRVVRFVRILRIFKL TRHFVGL | SEQ ID NO: 29 | FLLIIFLALGVL IFATMIYYA |
| Rattus norvegicus (rat) | SEQ ID NO: 30 | FLRVVRFVRILRIFKL TRHFVGL | SEQ ID NO: 31 | FLLIIFLALGVL IFATMIYYA |

FIG. 5B

```
KCNC1       1  ------------------------------------------
KCNC2       1  ------------------------------------------
KCNC3       1  MLSSVCVSSFRGRQGASKQQPAPPPQPPESPPPPPLPPQQQQPAQPGPAA
KCNC4       1  MISSVCVSSYRGRKSGNKP-------------------------------
consensus   1  ..............  ..

KCNC1       1  -----------------------MGQ----GDESERIVINVGGTRHQ
KCNC2       1  -----------------------MGK----IENNERVILNVGGTRHE
KCNC3      51  SPAGPPAPRGPGDRRAEPCPGLPAAAMGRHGGGGGDSGKIVINVGGVRHE
KCNC4      20  ----------------PSKTCLKEEMAK----GEASEKIIINVGGTRHE
consensus  51                      *..       .........****.**.

KCNC1      21  TYRSTLRTLPGTRLAWLA--------------------------------
KCNC2      21  TYRSTLKTLPGTRLALLASSEPPGDCLTTAGDKLQPSPPPLSPPPRAPPL
KCNC3     101  TYRSTLRTLPGTRLAGLT--------------------------------
KCNC4      49  TYRSTLRTLPGTRLAWLA--------------------------------
consensus 101  ******.********.*.

KCNC1      39  EPDAHSHF--------------DYDPRADEFFFDRHPGVFAHILNYYRT
KCNC2      71  SPGPGGCFEGGAGNCSSRGGRASDHPGGGREFFFDRHPGVFAYVLNYYRT
KCNC3     119  EPEAAARF--------------DYDPGADEFFFDRHPGVFAYVLNYYRT
KCNC4      67  DPDGGGRPETDGGGVGSSG----SSGGGGCEFFFDRHPGVFAYVLNYYRT
consensus 151  .*.......  ..  . .    ... ...************..******

KCNC1      74  GKLHCPADVCGPLYEEELAFWGIDETDVEPCCWMTYRQHRDAEEALDSFG
KCNC2     121  GKLHCPADVCGPLFEEELAFWGIDETDVEPCCWMTYRQHRDAEEALDIFE
KCNC3     154  GKLHCPADVCGPLFEEELGFWGIDETDVEACCWMTYRQHRDAEEALDSFE
KCNC4     113  GKLHCPADVCGPLFEEELTFWGIDETDVEPCCWMTYRQHRDAEEALDIFE
consensus 201  *************.****.**********.******************  *.

KCNC1     124  GAPLDNSADDADADGPGD------SGDGEDELEMT----KRLALSDS---
KCNC2     171  TPDLIG------------------GDPGDDEDLA---AKRLGIEDA-AG
KCNC3     204  APDPAGAANAANAAGAHDGGLDDEAGAGGGGLDGAGGELKRLCFQDAGGG
KCNC4     163  SPDGGG-----SGAGPSD-------EAGDDERELA---LQRLGPHEGGAG
consensus 251  .....  .  .....               . .........  ..**.. ......

KCNC1     161  ---PDGRPGG----FWRRWQPRIWALFEDPYSSRYARYVAFASLFFILVS
KCNC2     198  LGGPDGKSGR-----WRRLQPRMWALFEDPYSSRAARFIAFASLFFILVS
KCNC3     254  AGGPPGGAGGAGGTWWRRWQPRVWALFEDPYSSRAARYVAFASLFFILIS
KCNC4     198  HGAGSGGC--------RGWQPRMWALFEDPYSSRAARVVAFASLFFILVS
consensus 301  ....*.. ..      ..*..***.**********.**..********.*

KCNC1     204  ITTFCLETHERFNPIVNKTEIE-------NVRNGTQVRYYREAETEAFLT
KCNC2     243  ITTFCLETHEAFNIVKNKTE--------PVINGTSVVLQYEIETDPALT
KCNC3     304  ITTFCLETHEGFIHISNKTVTQASPIPGAPPENITNV----EVETEPFLT
KCNC4     240  ITTFCLETHEAFNIDRNVTEIL-------RVGNITSVHFRREVETEPILT
consensus 351  **********.*....*.*..           .. *  *.*.. .*.**...**

KCNC1     247  YIEGVCVVWFTFEFLMRVIFCPNKVEFIKNSLNIIDFVAILPFYLEVGLS
KCNC2     284  YVEGVCVVWFTFEFLVRIVFSPNKLEFIKNLLNIIDFVAILPFYLEVGLS
KCNC3     350  YVEGVCVVWFTFEFLMRITFCPDKVEFLKSSLNIIDCVAILPFYLEVGLS
KCNC4     283  YIEGVCVLWFTLEFLVRIVCCPDTLDFVKNLLNIIDFVAILPFYLEVGLS
consensus 401  *.*****.***.***.*....*  ...*.*. *****.************
```

FIG. 8A

```
KCNC1      297 GLSSKAAKDVLGFLRVVRFVRILRIFKLTRHFVGLRVLGHTLRASTNEFL
KCNC2      334 GLSSKAAKDVLGFLRVVRFVRILRIFKLTRHFVGLRVLGHTLRASTNEFL
KCNC3      400 GLSSKAAKDVLGFLRVVRFVRILRIFKLTRHFVGLRVLGHTLRASTNEFL
KCNC4      333 GLSSKAARDVLGFLRVVRFVRILRIFKLTRHFVGLRVLGHTLRASTNEFL
consensus  451 ******.*******************************************

KCNC1      347 LLIIFLALGVLIFATMIYYAERIGAQPNDPSASEHTHFKNIPIGFWWAVV
KCNC2      384 LLIIFLALGVLIFATMIYYAERVGAQPNDPSASEHTQFKNIPIGFWWAVV
KCNC3      450 LLIIFLALGVLIFATMIYYAERIGADPDDILGSNHTYFKNIPIGFWWAVV
KCNC4      383 LLIIFLALGVLIFATMIYYAERIGARPSDPRGNDHTDFKNIPIGFWWAVV
consensus  501 ********************.**.*.*.....**************

KCNC1      397 TMTTLGYGDMYPQTWSGMLVGALCALAGVLTIAMPVPVIVNNFGMYYSLA
KCNC2      434 TMTTLGYGDMYPQTWSGMLVGALCALAGVLTIAMPVPVIVNNFGMYYSLA
KCNC3      500 TMTTLGYGDMYPKTWSGMLVGALCALAGVLTIAMPVPVIVNNFGMYYSLA
KCNC4      433 TMTTLGYGDMYPKTWSGMLVGALCALAGVLTIAMPVPVIVNNFGMYYSLA
consensus  551 ************ *************************************

KCNC1      447 MAKQKLPKKKKKHIPRPPQLGSPNYCKSV---------------------
KCNC2      484 MAKQKLPRKRKKHIPPAPQASSPTFCKTE---------------------
KCNC3      550 MAKQKLPKKKNKHIPRPPQPGSPNYCKPDPPPPPPPHPHHGSGGISPPPP
KCNC4      483 MAKQKLPKKRKKHVPRPAQLESPMYCKSE---------------------
consensus  601 *******.*..**.*...*...**..**..

KCNC1      476 --------------------------------VNSPHHSTQSDTCPLA
KCNC2      513 --------------------------------LNMACNSTQSDTCLGK
KCNC3      600 ITPPSMGVTVAGAYPAGPHTHPGLLRGGAGGLGIMGLPPLPAPGEPCPLA
KCNC4      512 --------------------------------ETSPRDSTCSDTSPPA
consensus  651                                 .....  ..........

KCNC1      492 QEE-ILEINRA-------------------------------GRKPLRG
KCNC2      529 DNR-LLEHNRS-----------VLSGDDSTGSEPPL----SPPERLPIRR
KCNC3      650 QEE-VIEINRADPRPNGDPAAAALAHEDCPAIDQPAM---SPEDKSPITP
KCNC4      528 REEGMIERKRADSKQNGD-ANAVLSDEEGAGLTQPLASSPTPEERRALRR
consensus  701 ...  ..*...*..  ...  ....  .. ......

KCNC1      509 MSI-----------------------------------------------
KCNC2      563 SSTRDKNRRGETCFLLTTGDYTCASDGGIRKGYEKSRSLNNIAGLAGNAL
KCNC3      696 GS-RGRYSRDRACFLLT--DYAPSPDGSIRKATGAPPLPPQDWRKPGPPS
KCNC4      577 STTRDRNKKAAACFLLSTGDYACA-DGSVRKGTFVLRDL-----------
consensus  751 ..........   ..........   ........   ...   .

KCNC1          ------------------------
KCNC2      613 RLSPVTSPYNSPCFLRRSRSPIFSIL
KCNC3      743 FLPDLNANAAAWISP-----------
KCNC4      615 ---PLQHSPEAACPPTAGTLFLPH--
consensus  801 ....   ....         ..
```

FIG. 8B

COMPOSITIONS AND METHODS FOR SPINOCEREBELLAR ATAXIA

RELATED APPLICATIONS

This application is a continuation-in-part of U.S. application Ser. No. 11/411,233, filed Apr. 24, 2006, which claims the benefit of U.S. Provisional Patent Application Nos. 60/720,915, filed Sep. 26, 2005 and 60/674,182, filed Apr. 22, 2005. The entire teachings of the above applications are incorporated herein by reference.

GOVERNMENT SUPPORT

This invention was made with United States Government support under Grants No. R01GM43459, R01GM66686, R01N533123, T32GM065823 and R01NS33123 awarded by the National Institutes of Health. The United States Government has certain rights in this invention.

BACKGROUND OF THE INVENTION

The dominant spinocerebellar ataxias (SCA) are a growing group of heterogeneous neurodegenerative diseases with phenotypes consisting of cerebellar ataxia with or without extrapyramidal signs, dysarthria, occulomotor abnormalities, upper and lower motor neuron signs, cognitive decline, epilepsy, autonomic dysfunction, sensory deficits, and psychiatric manifestations. (Pulst, S. M., ed., "Genetics of Movement Disorders," Academic Press, San Diego (2003); Schols, L. et al., "Autosomal Dominant Cerebellar Ataxias: Clinical Features, Genetics, and Pathogenesis," *Lancet Neurol* 3(5):291-304 (2004), the entire content of each is incorporated herein by reference). A total of twenty-six loci are known, and for ten SCAs the causative gene or mutation has been determined. The majority of these are represented by abnormal CAG repeat expansions.

Despite the remarkable progress in identifying loci and genes for the dominant ataxias, approximately 40% of SCAs remain unaccounted for. Clinical characterization of the dominant SCAs is difficult, given both the degree of intra- and interfamilial variability and phenotypic similarity seen in mutations of different genes. (Mantuano, E., et al., "Spinocerebellar Ataxia Type 6 and Episodic Ataxia Type 2: Differences and Similarities Between Two Allelic Disorders," *Cytogenet Genome Res* 100(1-4):147-153 (2003); Gomez, C. M., and Subramony, S. H., "Dominantly Inherited Ataxias," *Semin Pediatr Neurol* 10(3):210-222 (2003), the entire content of each is incorporated herein by reference). Even for ataxias which share polyglutamine repeat expansions, in vivo and in vitro experiments have revealed remarkable differences in disease pathogenesis. (Ranum, L. P. and Day, J. W., "Myotonic Dystrophy: RNA Pathogenesis Comes Into Focus," *Am J Hum Genet* 74(5):793-804 (2004); Lieberman, A. P. and Fischbeck, K. H., "Triplet Repeat Expansion in Neuromuscular Disease," *Muscle Nerve* 23(6):843-850 (2000); Michalik, A. and Van Broeckhoven, C., "Pathogenesis of Polyglutamine Disorders: Aggregation Revisited," *Hum Mol Genet* 12(2):R173-R186 (2003), the entire content of each is incorporated herein by reference). The identification of mutations causing neurodevelopmental and neurodegenerative diseases and the elucidation of the molecular mechanisms by which they cause disease thus represents a major advance in the diagnosis and treatment of neurodegenerative and neurodevelopmental diseases.

SUMMARY OF THE INVENTION

The invention relates to a method of diagnosing neurodegenerative disease in an individual comprising analyzing a nucleic acid sample obtained from the individual for one or more mutations in the transmembrane domains of the KCNC3 gene resulting in a change in the output characteristics of fast spiking cerebellar neurons, wherein said mutation(s) results in neurodegenerative disease in the individual. Such mutations are referred to herein as "mutations of interest."

In one embodiment, the transmembrane domain is selected from the group consisting of the S2, S4 and S5 transmembrane domain (FIG. 5A).

In one embodiment, the S4 domain comprises amino acid sequence SEQ ID NO: 20.

In one embodiment, the S5 domain comprises amino acid sequence SEQ ID NO: 21.

In one embodiment, the S4 domain comprises nucleotide sequence SEQ ID NO: 22.

In one embodiment, the S5 domain comprises nucleotide sequence SEQ ID NO: 23.

In one embodiment, the S2 domain comprises amino acid sequence SEQ ID NO: 49.

In one embodiment, the S2 domain comprises nucleotide sequence SEQ ID NO: 50.

In another embodiment, the mutation is detected by dot blot hybridization.

In a further embodiments, the mutation is detected by southern blot hybridization.

In one embodiment, the mutation is detected by sequencing and in a particular embodiment the sample is amplified and the mutation is detected by sequencing said amplification product.

In another embodiment, the mutation causes an amino acid substitution in SEQ ID NO: 17 selected from the group consisting of R420H, R423H, R366H and F448L.

In a further embodiment, the mutation causes a nucleotide substitution in SEQ ID NO: 19 selected from the group consisting of guanine with adenine at nucleotide positions 1392, 1554 and 1563 and cytosine with adenine at nucleotide position 1639.

In one embodiment, the human has one or more of the following phenotypes selected from the group consisting of: epilepsy, mental retardation, cerebellar ataxia, extrapyramidal signs, dysarthria, oculomotor abnormalities, motor neuron signs, cognitive decline, autonomic dysfunction, sensory deficits and psychiatric manifestations.

In another embodiment, the neurodegenerative disease is spinocerebellar ataxia.

In a further embodiment, the spinocerebellar ataxia is spinocerebellar ataxia 13 (SCA13).

In another embodiment, the invention relates to a method of assessing an individual for the presence or absence of mutations of interest in the KCNC3 gene, wherein the KCNC3 gene without the mutations of interest comprises SEQ ID NO: 19, the method comprising assessing a nucleic acid test sample comprising the KCNC3 gene from the individual for the presence or absence of:
  a) a nucleotide substitution of guanine with adenine at nucleotide position 1554 in SEQ ID NO: 19;
  b) a nucleotide substitution of cytosine with adenine at nucleotide position 1639 in SEQ ID NO: 19
  c) a nucleotide substitution of guanine with adenine at nucleotide position 1563 in SEQ ID NO: 19; and
  d) a nucleotide substitution of guanine with adenine at nucleotide position 1392 in SEQ ID NO: 19.

In a further embodiment, the invention relates to a method of diagnosing neurodegenerative disease in an individual, comprising assessing a test sample from the individual for the presence of mutations of interest in the KCNC3 gene, wherein the mutations of interest are:
a) a nucleotide substitution of guanine with adenine at nucleotide position 1554 in SEQ ID NO: 19;
b) a nucleotide substitution of cytosine with adenine at nucleotide position 1639 in SEQ ID NO: 19;
c) a nucleotide substitution of guanine with adenine at nucleotide position 1563 in SEQ ID NO: 19; and
d) a nucleotide substitution of guanine with adenine at nucleotide position 1392 in SEQ ID NO: 19.
wherein the presence of any one of the mutations of interest is indicative of the presence of neurodegenerative disease.

In one embodiment, the test sample from the individual comprises a nucleic acid sample.

The accession code for the sequence of the potassium channel, voltage-gated, shaw-related subfamily member 3 (KCNC3) is NM_004977. The amino acid sequence is shown in SEQ ID NO: 17 and the nucleotide sequence is shown in SEQ ID NO: 19. As described herein, analysis of the KCNC3 gene revealed the following mutations: 1554G→A (R420H) in both Filipino and European pedigrees; 1639C→A (F448L) in French pedigrees; and 1563G→A (R423H) and 1392G→A (R366H) in European pedigrees, associated with neurodegenerative disease, and in particular with SCA13. These mutations are found in the transmembrane domains of the KCNC3 gene and result in abnormal or abrogated function of the encoded voltage-gated potassium channel. As a result of the invention described herein, new methods are available to detect neurodegenerative diseases in individuals.

BRIEF DESCRIPTION OF THE DRAWINGS

FIG. 3: Table 1: Clinical features in select affected family members (+-mild, ++-moderate, +++-severe).

FIG. 5A, Schematic of a single Kv3.3 subunit illustrating the six functional domains and re-entrant loop. Segments S1-S4 form the voltage sensor domain. Positively charged arginine residues in S4 sense changes in voltage. Segments S5, S6, and the re-entrant loop form the ion-selective pore. S5 forms the pore outer helix and functions to couple voltage-sensor conformational changes with pore opening and closing. SCA13 mutations are shown with arrows. FIG. 5B, Amino acid sequence comparison across species of the Kv3.3 S4 and S5 functional domains reveals 100% conservation. The box around the arginine indicates the R420H (S4) mutation and the box around the phenylalanine indicates the F448L (S5) mutation. The shading highlights the positively charged arginine residues occurring every third position.

FIGS. 8A and B: Sequence alignment of the KCNC family of voltage-gated potassium channels showing conservation of residues, including residues R420 and F448 in KCNC3. The KCNC1 amino acid sequence is shown in SEQ ID NO: 15, the KCNC2 amino acid sequence is shown in SEQ ID NO: 16, the KCNC3 amino acid sequence is shown in SEQ ID NO: 17 and the KCNC4 amino acid sequence is shown in SEQ ID NO: 18.

DETAILED DESCRIPTION OF THE INVENTION

Figure 1:
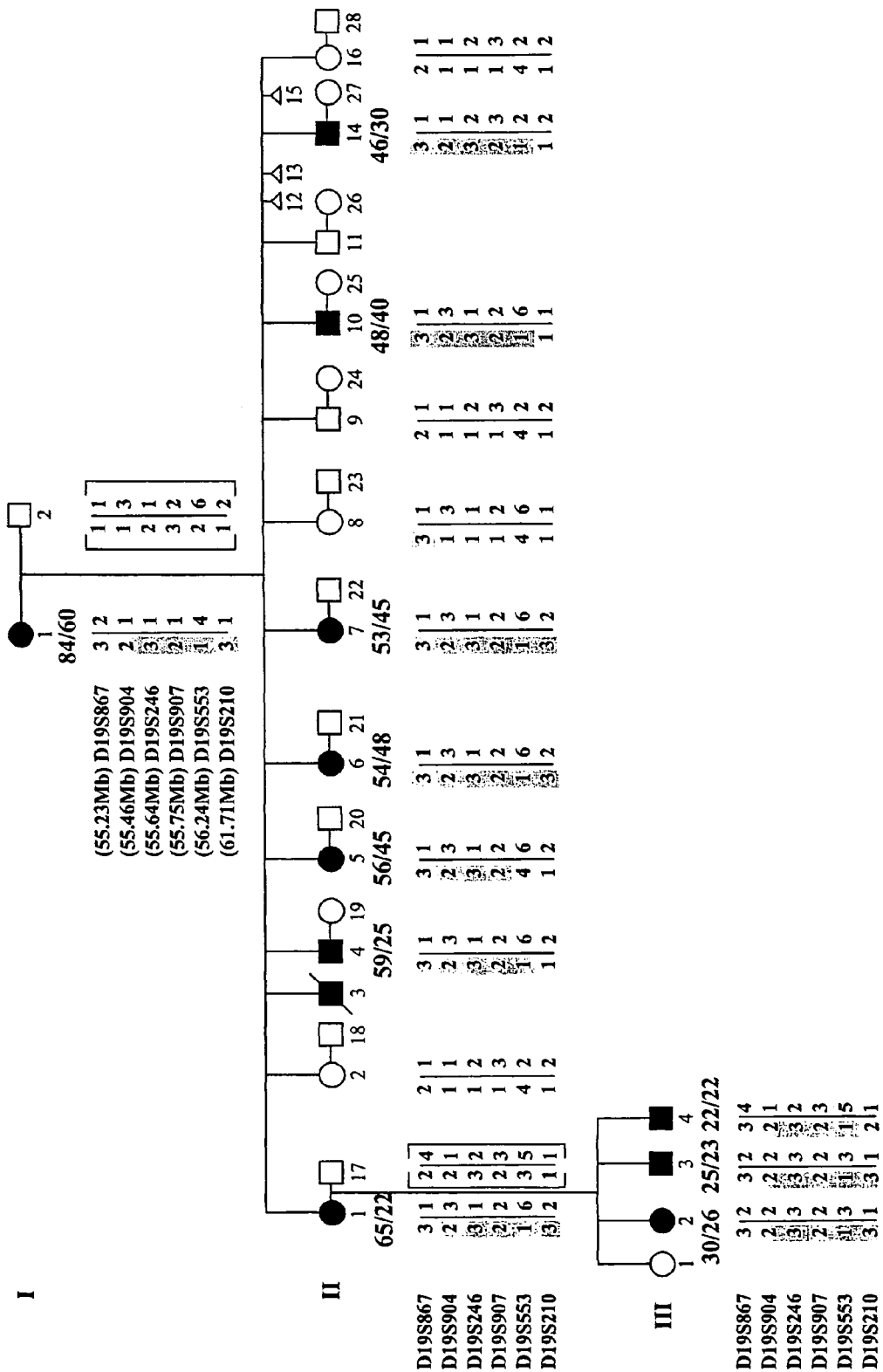
FIG. 1: Haplotypes for six informative chromosome 19 markers in the Filipino pedigree assuming the smallest number of recombination events. Note critical recombination events in individuals II-5 and II-8. Affected individuals are represented by darkened symbols. Age at examination and age-of-onset are shown in bold above the haplotype.

The present invention demonstrates for the first time that mutations in a voltage-gated potassium channel can cause developmental and degenerative neurological diseases. After evaluating a family pedigree with adult-onset ataxia, the causative mutation for a spinocerebellar ataxia was mapped to chromosome 19, locus q13, overlapping the SCA13 locus described in a French pedigree with childhood-onset mental retardation, ataxia, and seizures. Sequencing the gene revealed KCNC3 (Kv3.3), a voltage-gated Shaw potassium channel with enriched cerebellar expression, carrying the following mutations: 1554G→A (R420H) in both Filipino and European pedigrees; 1639C→A (F448L) in French pedigrees; and 1563G→A (R423H) and 1392G→A (R366H) in European pedigrees. The KCNC3 amino acid sequence is shown in SEQ ID NO: 17 and the corresponding nucleotide sequence is shown in SEQ ID NO: 19. Thus, the present invention provides for the identification of voltage-gated potassium channel mutations as a new class of genetic mutations involved in neurodegenerative diseases.

Because KCNC3 encodes a voltage-gated potassium channel belonging to the Shaw subfamily of K+ channels, it will now be possible to identify mutations in other voltage-gated potassium channels belonging to the same or related families of potassium channels, that are involved in neurodegenerative diseases. For example, the Shaker, Shab, Shaw, Shal families of voltage-gated potassium channels share significant homology throughout the functional domains that have been shown by the present invention to be involved in neurodevelopmental and neurodegenerative diseases. Thus, mutations in KCNA (Shaker): KCNA 1, 5 and 6 genes located in cluster on Chromosome 12p13, KCNA1 (Kv1.1), KCNA2 (Kv1.2), KCNA3 (Kv1.3), KCNA4 (Kv1.4), KCNA4L, KCNA5 (Kv1.5), KCNA6 (Kv1.6), KCNA7, KCNA8/KCNA9 (KCNQ1), KCNA10, KCNAB1 (Kv-β-1.1), KCNAB2 (Kv-β-1.2), KCNAB3, KCNB (Shab), KCNB1 (Kv2.1), KCNB2 (Kv2.2), KCNC (Shaw), KCNC1 (Kv3.1), KCNC2 (Kv3.2), KCNC3 (Kv3.3), KCNC4 (Kv3.4), KCND (Shal), KCND1 (Kv4.1), KCND2 (Kv4.2), KCND3 (Kv4.3) can now be detected and diagnosed in neurodevelopmental and neurodegenerative disease. All of the foregoing voltage-gated potassium channels are well known and their nucleotide and amino acid sequences are publicly available and can be found, for example, at http://www.ncbi.nlm.nih.gov. In addition, as shown in FIGS. 8A and B, the KCNC channels 1-4 share significant sequence homology with each other, including a large number of highly conserved residues, such as R420 and F448. In addition, some members of different voltage-gated potassium channel families interact with each other, as in heteromultimerization. For example, KCNC3 frequently heterodimerizes with other members of the KCNC family. Thus, mutations in functional domains of any of the closely related members of the KCNC family are predicted to produce phenotypes similar to those produced by the R420H, F448L, R423H and R366H mutations characterized herein. Dominant spinocerebellar ataxias (SCA) are a group of heterogeneous neurodegenerative diseases with phenotypes consisting of cerebellar ataxia, extrapyramidal signs, dysarthria, oculomotor abnormalities, motor neuron signs, cognitive decline, epilepsy, autonomic dysfunction, sensory deficits, and psychiatric manifestations.

The present invention provides a method of diagnosing neurodegenerative and/or neurodevelopmental disease in an individual by detecting a disease-associated mutation linked to a voltage-gated potassium channel locus. The disease-associated mutation can be linked to but outside a gene coding for a voltage-gated potassium channel or can be within the gene, such as in a coding sequence, 5' or 3' regulatory region, or within an intronic sequence.

As used herein, "coding sequence" refers to any DNA or RNA sequence that encodes genetic information, that is, the amino acid sequence of a protein or the nucleotide sequence of an RNA.

As used herein, "non-coding region" refers to a segment of DNA that does not comprise a gene and thus does not code for a protein.

As used herein, "synonymous changes" refer to the evolutionary substitution of one base for another in an exon of a gene coding for a protein, such that the amino acid sequence produced is not-modified.

In the methods of the invention, the disease-associated mutation can produce, for example, a functionally compromised gene product, including a dominant negative gene product. Examples of neurodevelopmental and neurodegenerative disease-associated mutations occurring within a voltage-gated potassium channel nucleotide sequence include the following mutations: 1554G→A (R420H) in both Filipino and European pedigrees; 1639C→A (F448L) in French pedigrees; 1563G→A (R423H) and 1392G→A (R366H) in European pedigrees, and analogous positions in related channels.

A variety of molecular methods useful in detecting a mutation in a voltage-gated potassium channel are well known in the art. For example, allele-specific oligonucleotide hybridization involves the use of a labeled oligonucleotide probe having a sequence perfectly complementary, for example, to a disease-associated sequence. Under appropriate conditions, the allele-specific probe hybridizes to a nucleic acid containing the disease-associated mutation but does not hybridize to the corresponding wild type nucleic acid sequence having one or more nucleotide mismatches. If desired, a second allele-specific oligonucleotide probe that matches the wild type sequence also can be used. Similarly, the technique of allele-specific oligonucleotide amplification can be used to selectively amplify, for example, a disease-associated polymorphic sequence by using an allele-specific oligonucleotide primer that is perfectly complementary to the nucleotide sequence of a disease-associated allele but which has one or more mismatches as compared to the corresponding wild type sequence (Mullis, et al. eds., "The Polymerase Chain Reaction," *Birkhauser*, Boston (1994), the entire content of which is incorporated herein by reference).

A heteroduplex mobility assay (HMA) is another well known assay that can be used to diagnose a neurodegenerative and/or neurodevelopmental disease caused by a mutation in a voltage-gated potassium channel according to a method of the invention. HMA is useful for detecting the presence of a polymorphic sequence since a DNA duplex carrying a mismatch, such as a heteroduplex between a wild type and mutated DNA fragment, has reduced mobility in a polyacrylamide gel compared to the mobility of a perfectly base-paired duplex (Delwart, E. L. t al., "Genetic Relationships Determined by a DNA Heteroduplex Mobility Assay: Analysis of HIV-1 env Genes," *Science* 262(5137):1257-1261 (1993); White, M. B. et al., "Detecting Single Base Substitutions as Heteroduplex Polymorphisms," *Genomics* 12(2):301-306 (1992), the entire content of each is incorporated herein by reference). The technique of single strand conformation polymorphism (SSCP) also can be used to detect the presence of a mutation in a voltage-gated potassium channel (Hayashi, K., "PCR-SSCP: A Simple and Sensitive Method for Detection of Mutations in the Genomic DNA," *PCR Methods Applic.* 1(1):34-38 (1991), the entire content of which is incorporated herein by reference). This technique can be used to detect mutations based on differences in the secondary structure of single-strand DNA that produce an altered electrophoretic mobility upon non-denaturing gel electrophoresis.

Denaturing gradient gel electrophoresis (DGGE) also can be used to detect a mutation in a voltage-gated potassium channel. In DGGE, double-stranded DNA is electrophoresed in a gel containing an increasing concentration of denaturant; double-stranded fragments made up of mismatched wild type and disease-associated sequences have segments that melt more rapidly, causing such fragments to migrate differently as compared to perfectly complementary sequences obtained from normal individuals (Sheffield, V. C. et al., "Identifying DNA Polymorphisms by Denaturing Gradient Gel Electrophoresis" in *PCR Protocols: A Guide to Methods and Applications*, Innis, M. A. (ed.) pp. 206-218 (1990), the entire content of which is incorporated herein by reference).

Other well-known approaches for analyzing a mutation include automated sequencing, RNAase mismatch techniques (Winter, E. et al., "A Method to Detect and Characterize Point Mutations in Transcribed Genes: Amplification and Overexpression of the Mutant c-Ki-ras Allele in Human Tumor Cells," *Proc. Natl. Acad. Sci.* 82:7575-7579 (1985), the entire content of which is incorporated herein by reference) and the use of restriction fragment length polymorphisms (*PCR Protocols: A Guide to Methods and Applications*, Innis, M. A. (ed.) (1990), the entire content of which is incorporated herein by reference). For families in which the disease-associated mutation has been defined, automated sequencing of the region of interest can be particularly useful in diagnosing a neurodegenerative or neurodevelopmental disease. In addition, dot-blot hybridization, RFLP analysis and many more techniques well known in the art can be used for the purposes of the present invention.

The present invention identifies KCNC3 mutations as causative for SCA13 and demonstrates the importance of voltage-gated potassium channels in phenotypes ranging from developmental disorders to late-onset neurodegenerative disease. It is likely that in vivo systems will be able to assess the consequences of mutant KCNC3 on three distinct but interrelated functions: cerebellar development, cerebellar function in the mature organism and the role of proper channel function preventing neuronal death. Both mutations show some intra-familial phenotypic variability highlighting the importance of compensatory mechanisms and the likely presence of other genetic and environmental modifiers. Further understanding of the role of voltage-gated K channels in cerebellar degeneration may lead to therapies aimed at modulating channel function to both restore cerebellar function and reduce neurodegeneration.

The following examples are provided to better illustrate the claimed invention and are not to be interpreted as limiting the scope of the invention. To the extent that specific materials are mentioned, it is merely for the purpose of illustration and is not intended to limit the invention. One skilled in the art may develop equivalent means or reactants without the exercise of inventive capacity and without departing from the scope of the invention.

EXAMPLE 1

Patients:

A large Filipino family segregating a dominant trait for cerebellar ataxia was available for examination. There are eleven affected individuals spanning three generations. The living affecteds include the matriarch, eight individuals in generation two, and three individuals in generation three. In addition, there are five unaffected individuals in generation two, with one presumed unaffected and thirty-nine at-risk individuals in generation three, who have not yet been examined. After written informed consent was obtained, blood was collected and DNA extracted from fifteen family members. One affected individual from generation three was available for brain CT imaging.

Mutation and Linkage Analyses:

Mutations in SCA1, 2, 3, 6, 7, 8, 12, 17, and DRPLA genes were eliminated as potential etiologies by direct PCR analysis (Pulst, S. M., "Neurogenetics: Single Gene Disorders," *J Neurol Neurosurg Psych* 74(12):1608-1614 (2003), the entire content of which is incorporated herein by reference). For SCA10, which has an expansion mutation that cannot be amplified by PCR, two normal alleles were observed in all affected individuals (Matsuura T., et al., "Large Expansion of the ATTCT Pentanucleotide Repeat in Spinocerebellar Ataxia Type 10," *Nat Genet* 26(2):191-194 (2000), the entire content of which is incorporated herein by reference). Linkage to loci for SCA5, 11, 13, 14, 16, 18, 19, 21, 23, and 25 were excluded by the observation of recombination events in close proximity to these loci.

In the genome-wide screen for linkage, a total of 377 fluorescent-tagged microsatellite markers in the human ABI Linkage Set v2.5 were utilized. These markers cover the entire genome with an average inter-marker genetic distance of 10 cM. Markers were run on an ABI 3100 using a capillary system.

To evaluate linkage in the 19q13 region, additional screening was done on the matriarch, eight affecteds and five unaffecteds in generation two, and three affected individuals in generation three as previously described (Zu L., "Mapping of a New Autosomal Dominant Spinocerebellar Ataxia to Chromosome 22," *Am J Hum Genet* 64(2):594-599 (1999), the entire content of which is incorporated herein by reference). High resolution mapping was performed utilizing dinucleotide repeat markers obtained in the region of 19q13 from the Ensembl genome browser (http://www.ensembl.org, Jan. 15, 2005).

PCR was performed in a 20 µl reaction containing 100 ng of genomic DNA template, 100 pmol of each primer, 2.5 mM each dNTP, 2.5 mM MgCl2, 0.25 U Taq polymerase, and buffer supplied by the vendor. The upstream primer was end-labeled with $\gamma^{32}$P-ATP utilizing T4 Polynucleotide Kinase (Promega catalog #M4101) according to the manufacturer's instructions prior to PCR. The reaction conditions were as follows: initial denaturation at 95° C. for five minutes; 35 cycles of denaturing at 95° C. for 30 s, annealing at 62° C. for 30 s, and extension at 72° C. for 40 s; and a final extension at 72° C. for ten minutes. The entire reaction was performed in an M. J. Research PTC 200 thermocycler. The PCR products were analyzed by electrophoresis on a 6% denaturing polyacrylamide gel (National Diagnostics, Atlanta, Ga.) on an IBI BaseRunner 200 sequencer. Gels were exposed to Hyperfilm MP (Amersham Biosciences, England) and developed with a Kodak X-Omat automated processor.

Statistical Analysis:

Pair-wise and multi-point linkage analyses were performed with Genehunter (Kruglyak, L. and Lander, E. S., "Faster Multipoint Linkage Analysis using Fourier Transformations," *J Comput Biol* 5(1):1-7 (1998); Kruglyak, L., et al., "Parametric and Nonparametric Linkage Analysis: A Unified Multipoint Approach," *Am J Hum Genet* 58(6):1347-1363 (1996)) under the assumption of autosomal dominant inheritance and a disease allele frequency of 0.001 with penetrance set at 95 or 99%. The program size parameter (max bits) was fixed so that all genotyped subjects were included in the analyses. Genehunter also generated nonparametric results which were not substantively different from the parametric results presented here.

Results:

Clinical features of the family. Nineteen individuals in the extended kindred were examined. Ten clinically affecteds from three generations were available for examination. The proband, an 82 year-old female is the oldest affected with disease onset at age 60 years. She has twelve living children: seven females of which four are affected, and five males of which three are affected. The seven affected offspring in generation two are between 46 and 65 years old, with age of onset ranging from 22 to 48 years (mean 36.4 years). The third generation has three affected individuals with mean onset at age 24.5 years. This includes a: 30 year-old female (onset age 26), 25 year-old male and a newly symptomatic male (onset ages 23 and 22 respectively). Cerebellar signs noted among the ten affecteds included gait ataxia, limb ataxia/dysmetria, titubation, hypotonia, dysarthria, and nystagmus. Two have mild, symmetric hyper-reflexia with no Babinski sign. Duration of disease ranges from 1-43 years with a mean of 13 years. The three oldest affecteds have the most severe ataxia (2 are wheelchair bound) with a disease duration of 24, 43, and 34 years, respectively. CT brain imaging (performed within the first year of symptoms) of the 30 year-old third generation female demonstrated mild cerebellar atrophy.

Exclusion of Known Loci:

DNA repeat expansion mutations in SCA1, 2, 3, 6, 7, 8, 12, 17, and DRPLA were excluded by direct PCR analysis. Pentanucleotide repeat expansions in the SCA10 gene were excluded by demonstration of heterozygosity for two normal alleles in affecteds. Other SCA loci were excluded by linkage analysis. This included analysis with markers linked to SCA5, 11, 13, 14, 16, 18, 19, 21, 23, and 25. For each locus, at least one recombination event was observed within the linked region and for markers flanking the region.

Genome-Wide Screen:

Due to the structure of the pedigree, approximately 15% of markers were non-informative as heterozygosity in individual I:2 was required for informativeness in generation II. Given this limitation, the results of the initial scan left several large gaps in the genome due to adjacent non-informative markers. Therefore, four genome areas (chromosomes 1, 14, 19, and 22) were further screened with CA repeat markers obtained from the Ensembl Genome Browser (http://www.ensembl.org, date of accession: Jan. 15, 2005).

After linkage to chromosomes 1, 14, and 22 was excluded was re-examined linkage to the 19p13 region, as the genome scan failed to provide information in a large region defined by D19S902 at 53.02 Mb, and D19S210 at 61.71 Mb. This region was of interest as spinocerebellar ataxia type 13 had previously been mapped to 19q13.3-q13.4 in a large French family (Herman-Bert, A., et al., "Mapping of Spinocerebellar Ataxia 13 to Chromosome 19q13.3-q13.4 in a Family with Autosomal Dominant Cerebellar Ataxia and Mental Retardation," *Am J Hum Genet* 67(1):229-235 (2000), the entire content of which is incorporated herein by reference). The genome scan identified several recombination events in affected individuals at D19S210 and one recombination in a generation II unaffected individual at marker D19S902.

Haplotypes for additional informative markers are shown in FIG. 1. Several markers including D19S904 showed no recombination events in affected or unaffected individuals. Obligate recombinants were detected for both D19S867 and D19S553. These markers define a physical candidate region of 1 Mb.

Figure 2:
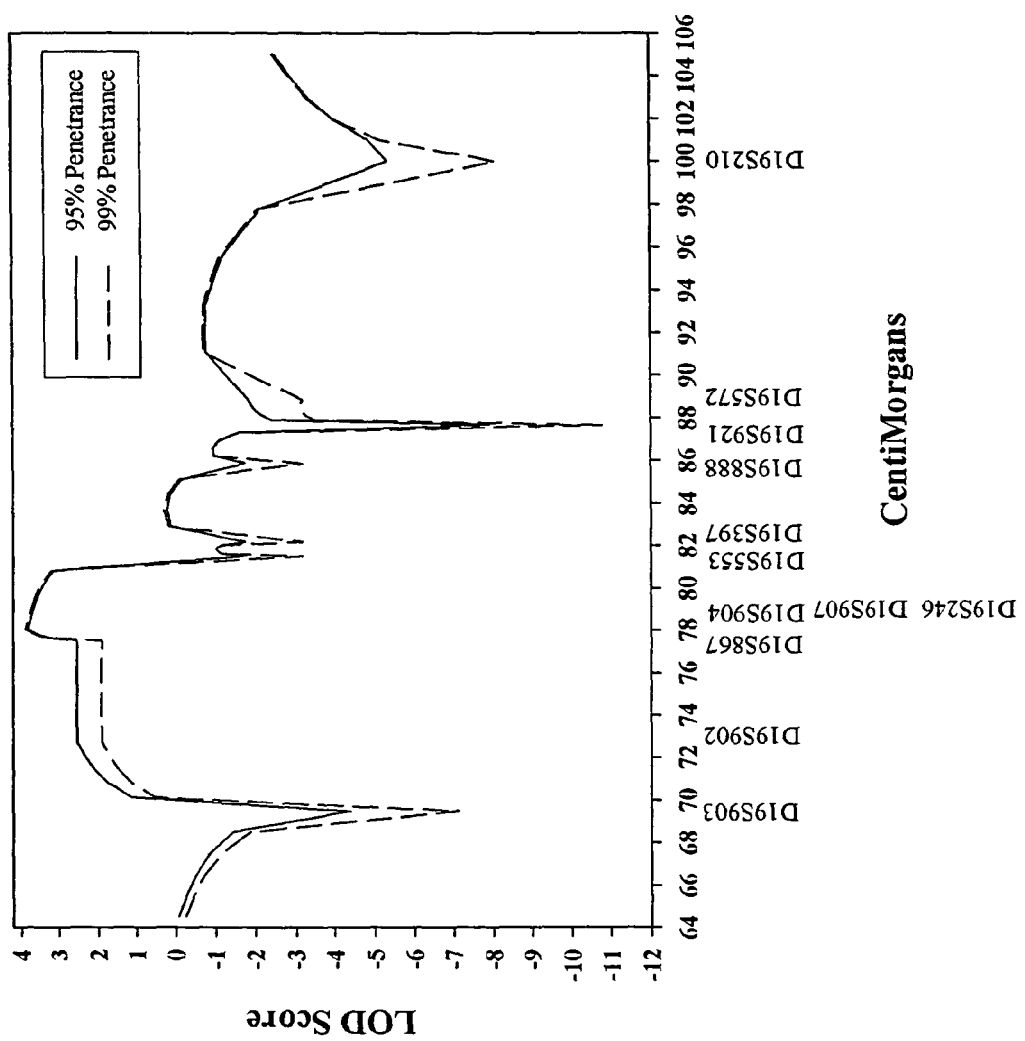
FIG. 2: Multipoint linkage analysis with twelve chromosome 19 markers. Max LOD is 3.83 at 78 cM. Linkage analysis performed assuming autosomal dominant inheritance with an allele frequency of 0.001 and 95% (solid line) or 99% (dashed line) penetrance. The genetic distances are based on the Marshfield genetic map.

The formal multi-point linkage analysis is shown in FIG. 2. The LOD-1 drop interval provides a most probable location of the disease gene in a 4 cM region near D19S904.

FIG. 3 is a table showing the clinical features in select affected family members (+-mild, ++-moderate, +++-severe).

Discussion:

The clinical phenotype of SCA13 is based on observations in one pedigree of French origin (Herman-Bert, A., et al., "Mapping of Spinocerebellar Ataxia 13 to Chromosome 19q13.3-q13.4 in a Family with Autosomal Dominant Cerebellar Ataxia and Mental Retardation," *Am J Hum Genet* 67(1):229-235 (2000), the entire content of which is incorporated herein by reference). Onset was in childhood and patients had mild mental retardation, and a relatively pure cerebellar ataxia with dysarthria, nystagmus, and discrete pyramidal features. The locus for this SCA spans an 8 cM region on 19q13.3-13.4 from 50.64-56.24 Mb (Généthon and Center for Medical Genetics, Marshfield Medical Research Foundation genetic maps) (Dib, C., et al., "A Comprehensive Genetic Map of the Human Genome Based on 5,264 Microsatellites," *Nature* 380(6570):152-154 (1996); Broman, K. W., et al., "Comprehensive Human Genetic Maps: Individual and Sex-Specific Variation in Recombination," *Am J Hum Genet* 63(3):861-869 (1998), the entire content of each is incorporated herein by reference). The disease gene in the Filipino pedigree in this report maps to the distal segment of the SCA13 candidate region between genetic markers located at 55.46 and 56.24 Mb of the chromosome 19 genomic sequence.

Though the mechanism for disease in the majority of described SCAs is trinucleotide repeat expansion, evidence for clear anticipation is lacking in the description of the French SCA13 pedigree. Furthermore, neither rapid expansion detection (RED) analysis (Zander, C., et al., "Multivariate Analysis of Factors Influencing Repeat Expansion Detection," *Genome Res* 8(10):1085-1094 (1998), the entire content of which is incorporated herein by reference) or Western blotting with an antibody which selectively recognizes polyglutamine sequences (Trottier, Y., et al., "Polyglutamine Expansion as a Pathological Epitope in Huntington's Disease and Four Dominant Cerebellar Ataxias," *Nature* 378(6555):403-406 (1995), the entire content of which is incorporated herein by reference) found evidence for CAG expansion (commonly seen in diseases with anticipation) in SCA13. The Filipino pedigree shows evidence of anticipation with mean age-of-onset falling from 36 years in generation II to 24 years in generation III. However, caution must be exercised in interpreting this finding as the number of observations in the individual pedigree is small. Moreover, anticipation has been described in Hereditary Spastic Paraplegia 4, in which the mutational event is not a pathological repeat expansion (Raskind, W. H., et al., "Familial Spastic Paraparesis: Evaluation of Locus Heterogeneity, Anticipation, and Haplotype Mapping of the SPG4 Locus on the Short Arm of Chromosome 2," *Am J Med Genet* 74(1):26-36 (1997), the entire content of which is incorporated herein by reference). Examination of the approximately million base-pair genomic sequence in the region defined by our family also failed to reveal areas of greater than ten uninterrupted CAG repeat tracts.

Surprisingly the SCA13 locus on CHR19q was initially excluded based on the observation of several recombination events. In retrospect, it is evident that the chromosomal region shared by all affected individuals is unusually small. This made initial detection of linkage difficult, but resulted in an unusually small candidate region. Genes in the overlapping region defined by us and Herman-Bert, A. et al., "Mapping of Spinocerebellar Ataxia 13 to Chromosome 19q13.3-q13.4 in a Family with Autosomal Dominant Cerebellar Ataxia and Mental Retardation," *Am. J. Hum. Genet.* 67(1):229-235 (2000), the entire content of which is incorporated herein by reference) have been identified as potential candidates. These include genes belonging to families of transcription factors, trafficking proteins, and ion channels.

Assuming that the French SCA13 mutation and the mutation in the Filipino family are allelic, the results would greatly narrow the SCA13 candidate region. However, marked differences distinguish the previously described SCA13 phenotype and the phenotype in the Filipino pedigree, described herein. These include a much lower age of onset in SCA13 and mental retardation described in the French pedigree. In addition, there is the suggestion of anticipation in the Filipino family described here. Due to the rather invariant phenotypes described within the two families, the favored explanations are mutations in two distinct genes or allelic heterogeneity. Given the size of the SCA13 region it is possible that the causative genes are different in these two conditions. A similar phenomenon has been suggested in SCA15, where several overlapping loci lead to similar though clinically distinct phenotypes (Dudding, T. E., et al., "Autosomal Dominant Congenital Non-Progressive Ataxia Overlaps with the SCA15 Locus," *Neurology* 63(12):2288-2292 (2004), the entire content of which is incorporated herein by reference). Alternatively, the phenotypic differences may represent allelic heterogeneity or identical mutations with the observed differences due either to genetic background or environmental factors. Allelic heterogeneity has been well-described in SCA14 and includes disparate phenotypes such as early onset with mental retardation and pure late-onset cerebellar ataxia, reminiscent of the two phenotypes in the French and Filipino pedigrees mapping to 19q13 (Stevanin, G., et al., "Mutation in the Catalytic Domain of the Protein Kinase C γ and Extension of the Phenotype Associated with Spinocerebellar Ataxia Type 14," *Arch Neurol* 61(8):1242-1248 (2004); Chen, D. H., et al., "The Clinical and Genetic Spectrum of Spinocerebellar Ataxia 14," *Neurology* 64(7):1258-1260 (2005), the entire content of which is incorporated herein by reference).

EXAMPLE 2

Patients:

A Filipino family segregating a dominant trait for cerebellar ataxia was examined. There were eleven affected individuals including the proband, seven individuals in generation two, and three individuals in generation three. In addition, there were five unaffected individuals in generation two, with one unaffected and nineteen at-risk individuals in generation three. Blood was collected and DNA extracted from fifteen family members after informed consent was obtained.

Mutation and Linkage Analyses:

To further evaluate linkage in the 19q13 region, additional markers were typed in the proband, seven affecteds and four unaffecteds in generation two, and three affecteds in generation three. High-resolution mapping was performed by PCR amplification of dinucleotide repeat markers obtained in the region of 19q13 from the Ensembl genome browser (release 31.35d). The PCR products were analyzed by electrophoresis on a 6% denaturing polyacrylamide gel.

Sequence Analysis:

DNA sequencing was performed using the ABI (Foster City, Calif.) "BigDye Terminator v3.1" cycle sequencing kit and the following protocol. To 5 ng (5 µl) purified PCR amplicon, 4 µl reaction pre-mix, 2 µl 5× sequencing buffer, 3.2 pmol (2 µl) appropriate primer, and 7 µl deionized water were added to a 96-well microtitre plate and transferred to PCR thermocycler (MJ Research PTC-200) and cycled as follows: 1) 96° C. for 1 minute, 2) 96° C. for 10 seconds to 50° C. for 5 seconds to 60° C. for 4 minutes×25 cycles. Sequencing products were then purified using ABI Centri-Sep™ spin columns. Resuspended samples were then electrophoresed on a 4.5% acrylamide gel in an ABI 377 DNA sequencer according to the manufacture's protocol. All sequences were analyzed using BioEdit's biological sequence alignment editor version 5.0.9.1. Sequencing primers as follows:

```
SEQ ID NO: 1:
Exon 1-5'TAG GTG AGG GCG TGC GAT CTG TT

SEQ ID NO: 2:
3'GCC CGC GGA AGG ACG AGA C

SEQ ID NO. 3:
5'CTC CCA CCC AAT CCC GTC GGT C

SEQ ID NO. 4:
3'GCG ATG CTG CCG GTA GGT CAT CC

SEQ ID NO. 5:
5'TTC GCG TAC GTG CTC AAC TAC TA

SEQ ID NO. 6:
3'TGG GGA AGA GGC TTC TAG GAG

SEQ ID NO. 7:
Exon 2-5'GGG CAC TGG AAG GGT CTT

SEQ ID NO. 8:
3'ATG GGG ATG TTC TTG AAG TAG GT

SEQ ID NO. 9:
5'CGC CAC CAT GAT TTA CTA CGC

SEQ ID NO. 10:
3'TTT TTC TCC CTC ACC TCT TCG AC

SEQ ID NO. 11:
Exons 3/4-5'ATC TTG CCC CAC CGC GTG TTC A

SEQ ID NO. 12:
3'CGG TCA GTG GGG GCT GCA TGT TC

SEQ ID NO. 13:
Exon 5-5'GAA ATG ATC CCG GCG GCG TTT CT

SEQ ID NO. 14:
3'GGC AGC AAG GCG GGA TGG TG
```

Electrophysiology:

The coding region of a human Kv3.3 cDNA clone (Rae, J. L., and Shepard, A. R., "Kv3.3 Potassium Channels in Lens Epithelium and Corneal Endothelium," *Exp. Eye. Res.* 70(3): 339-348 (2000), the entire content of which is incorporated herein by reference) was transferred into the Bluescript II SK vector. RNA was transcribed and injected into Xenopus oocytes for two electrode voltage clamp analysis using standard methods (Silverman, W. R., et al., "Mg (2+) Modulates Voltage-Dependent Activation in Ether-a-go-go Potassium Channels by Binding Between Transmembrane Segments S2 and S3," *J. Gen. Physiol.* 116(5):663-678 (2000), the entire content of which is incorporated herein by reference). Currents were recorded 48 to 72 h post injection in a bath solution containing 4 mM KCl, 85 mM NaCl, 1.8 mM $CaCl_2$, 10 mM HEPES, pH 7.2. To record tail currents, the bath solution was switched to 89 mM RbCl, 2.4 mM $NaHCO_3$, 0.82 mM $Ca(NO_3)_2$, 0.41 mM $CaCl_2$, 10 mM HEPES, pH 7.2. For dominant negative experiments, 1 ng of Kv3.3 or Shaker IR RNA was injected, in the absence or presence of the indicated ratio of mutant RNA.

Figure 4:
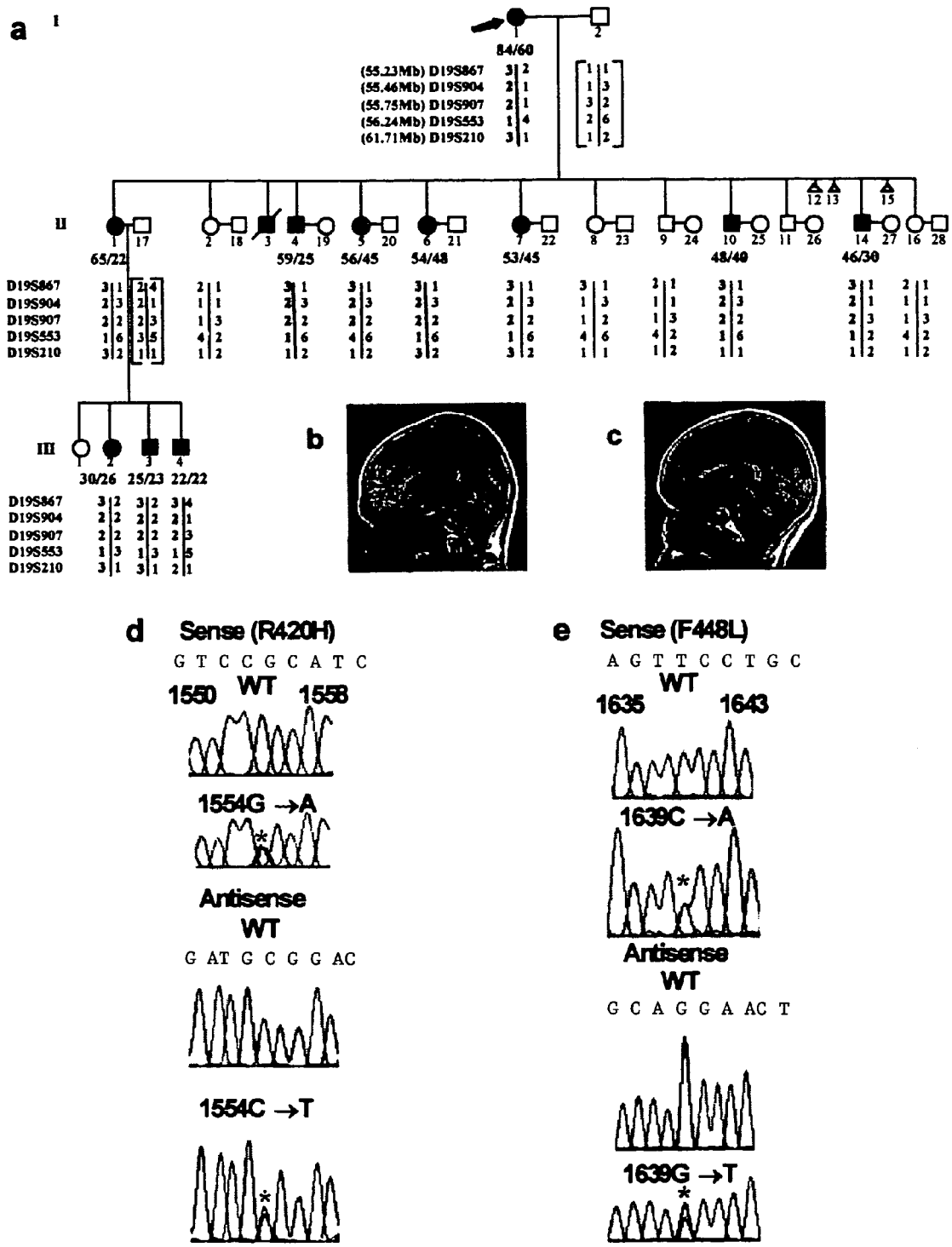
FIGS. 4A-E: Filipino pedigree with autosomal dominant spinocerebellar ataxia. a, Filipino pedigree and haplotypes for five informative chromosome 19 markers assuming the smallest number of recombination events. Note critical recombination events in individuals II-5 and II-8. Haplotype blocks segregating with disease are shaded. Affected individuals are represented by darkened symbols. Age at examination and age-of-onset are shown in bold above the haplotype. Proband denoted by arrow. Sagittal T1 sequence MR images of individuals III-2 (b) and II-1 (c) reveal marked cerebellar volume loss. Duration of disease is 16 years in III-2 and 43 years in II-1, likely accounting for the more pronounced degeneration in II-1. d, and e, DNA sequence analysis revealed the 1554G→A, and 1639C→A point mutations in SEQ ID NO: 19 in exon 2 of Kv3.3 causing SCA13. Both sense and anti-sense strands are shown, as well as wild-type (WT) sequence. Mutations designated with asterisk.

Results:

A three-generation Filipino family segregating an adult-onset dominant ataxia with prominent cerebellar signs and symptoms (Waters, M. F. et al., "An Autosomal Dominant Ataxia Maps to 19q13: Allelic Heterogeneity of SCA13 or Novel Locus?," *Neurology* 65(7):1111-1113 (2005), the entire content of which is incorporated herein by reference) as well as cerebellar atrophy on magnetic resonance imaging (FIGS. 4b and c) has previously been identified as discussed in Example 1. The clinical and imaging phenotypes were typical of degenerative SCAs. A genome-wide linkage scan revealed a disease locus in a ~4 cM region of 19g13, with a 3.89 LOD score. This region partially overlapped the SCA13 locus (Herman-Bert, A., et al., "Mapping of Spinocerebellar Ataxia 13 to Chromosome 19q13.3-q13.4 in a Family with Autosomal Dominant Cerebellar Ataxia and Mental Retardation," *Am J Hum Genet* 67(1):229-235 (2000), the entire content of which is incorporated herein by reference) mapped in a French pedigree with mild mental retardation, early-onset ataxia, and slow progression, though the Filipino phenotype was clinically distinguishable from SCA 13. Through high-resolution mapping, the linkage region was reduced to ~900K bases. Haplotypes are shown in FIG. 4a. Several markers including D19S904 showed no recombination events. Obligate recombinants were detected for both D19S867 and D19S553, which defined a physical candidate region with the LOD-1 drop interval providing a probable location of the disease gene near D19S904.

This region contained approximately forty candidate genes, including KCNC3. Direct sequencing revealed two missense mutations in exon 2. The Filipino pedigree contained 1554G→A, encoding R420H in the third conserved arginine residue in S4 (FIG. 4d). The French pedigree contained 1639C→A, encoding F448L near the cytoplasmic end of S5 (FIG. 4e).

Discussion:

Dominant spinocerebellar ataxias (SCA) are heterogeneous neurological diseases with phenotypes consisting of cerebellar ataxia, extrapyramidal signs, dysarthria, oculomotor abnormalities, motor neuron signs, cognitive decline, epilepsy, autonomic dysfunction, sensory deficits, and psychiatric manifestations (Pulst, S. M. ed., "Genetics of Movement Disorders," *Academic Press, San Diego (*2002); Schols, L. et al., "Autosomal Dominant Cerebellar Ataxias: Clinical Features, Genetics, and Pathogenesis," *Lancet Neurol* 3(5):291-304 (2004), the entire content of each is incorporated herein by reference). Twenty-six SCA loci are described, and for ten the causative gene or mutation has been determined. Little is known about the normal function of most SCA genes, though the majority represent polyglutamine (polyQ) expansion diseases.

Figure 5A:
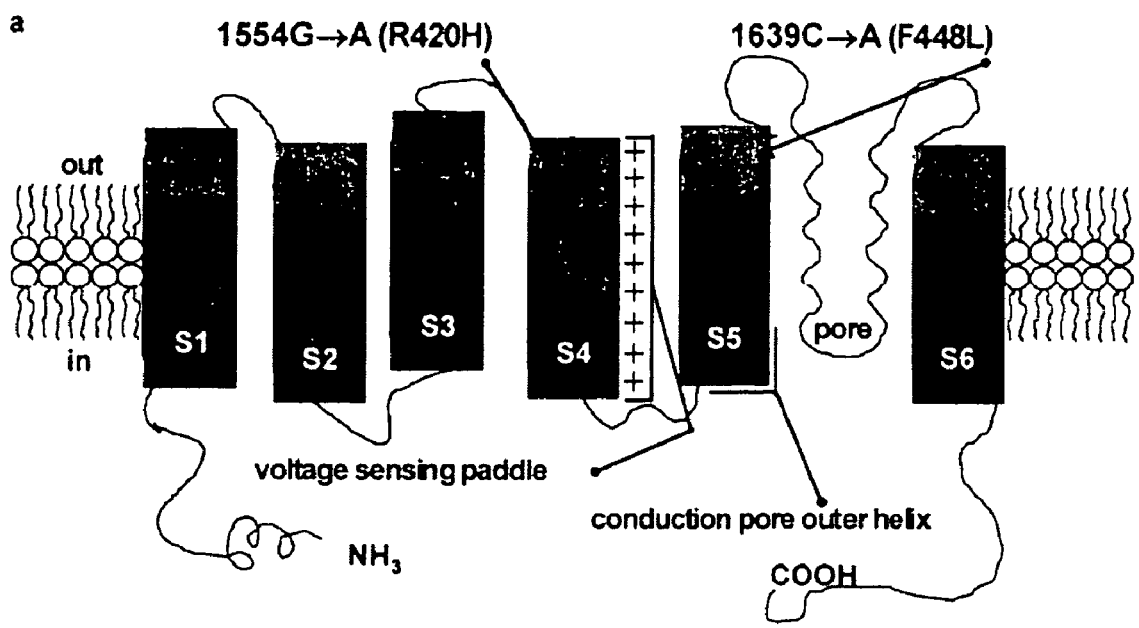
FIGS. 5A and B: Functional motifs and sequence comparisons of Shaw-subfamily voltage-gated potassium channels.

Among voltage-gated $K^+$ channels, the functional properties of Kv3 channels are distinct. Kv3 channels activate in a more depolarized range and close much more rapidly compared to other Kv channels (Rudy, B. and McBain, C. J., "Kv3 Channels: Voltage-Gated K+ Channels Designed for High-Frequency Repetitive Firing," *Trends Neurosci.* 24(9):517-526 (2001); Ghanshani, S. et al., "Genomic Organization, Nucleotide Sequence, and Cellular Distribution of a Shaw-Related Potassium Channel Gene, Kv3.3, and Mapping of Kv3.3 and Kv3.4 to Human Chromosomes 19 and 1," *Genomics* 12(2):190-196 (1992), the entire content of each is incorporated herein by reference). These properties facilitate high frequency firing of action potentials with little or no adaptation, a characteristic of neuronal populations found in the mammalian neocortex, hippocampus, auditory nuclei, and cerebellum (Ghanshani, S. et al., "Genomic Organization, Nucleotide Sequence, and Cellular Distribution of a Shaw-Related Potassium Channel Gene, Kv3.3, and Mapping of Kv3.3 and Kv3.4 to Human Chromosomes 19 and 1," *Genomics* 12(2):190-196 (1992), the entire content of which is incorporated herein by reference). Like other voltage-gated $K^+$ channels, Kv3 channels are tetramers. Different Shaw family subunits are able to co-assemble with each other, but not with subunits from other Kv subfamilies (Covarrubias, M., et al. "Shal, Shab, and Shaw Express Independent K+ Current Systems," *Neuron* 7(5):763-773 (1991); Shen, N. V. and Pfaffinger, P. J., "Molecular Recognition and Assembly Sequences Involved in the Subfamily-Specific Assembly of Voltage-Gated K+ Channel Subunit Proteins," *Neuron* 14(3): 625-633 (1995); Aggarwal, S. K. and MacKinnon, R., "Contribution of the S4 Segment to Gating Charge in the Shaker K+ Channel," *Neuron* 16(6):1169-1177 (1996); Pulst, S. M., ed. "Genetics of Movement Disorders," *Academic Press, San Diego (*2003), the entire content of each is incorporated herein by reference). Each subunit has six transmembrane segments and a re-entrant loop (FIG. 5a). The first four transmembrane segments, S1-S4, constitute the voltage sensor domain, whereas the last two segments, S5 and S6, and the re-entrant loop form the ion-selective pore (Long, S. B., et al., "Crystal Structure of a Mammalian Voltage-Dependent Shaker Family K+ Channel," *Science* 309(5736):897-903 (2005); Schols, L. et al., "Autosomal Dominant Cerebellar Ataxias: Clinical Features, Genetics, and Pathogenesis," *Lancet Neurol* 3(5): 291-304 (2004), the entire content of each is incorporated herein by reference). The Filipino mutation is located in S4, the main voltage-sensing element and changes one of the multiple positively charged residues that respond to changes in membrane potential (Aggarwal, S. K. and MacKinnon, R., "Contribution of the S4 Segment to Gating Charge in the Shaker K+ Channel," *Neuron* 16(6):1169-1177 (1996); Seoh, S. A., et al., "Voltage-Sensing Residues in the S2 and S4 Segments of the Shaker K+ Channel," *Neuron* 16(6): 1159-1167 (1996); Waters, M. F. et al., "An Autosomal Dominant Ataxia Maps to 19q13: Allelic Heterogeneity of SCA13 or Novel Locus?," *Neurology* 65(7):1111-1113 (2005); and Rudy, B. and McBain, C. J., "Kv3 Channels: Voltage-Gated K+ Channels Designed for High-Frequency Repetitive Firing," *Trends Neurosci.* 24(9):517-526 (2001), the entire content of each is incorporated herein by reference). The French mutation is in the cytoplasmic end of S5 (FIG. 5a), which is involved in coupling voltage-sensor conformational changes with opening and closing of the pore (Covarrubias, M., et al.

Figure 6:
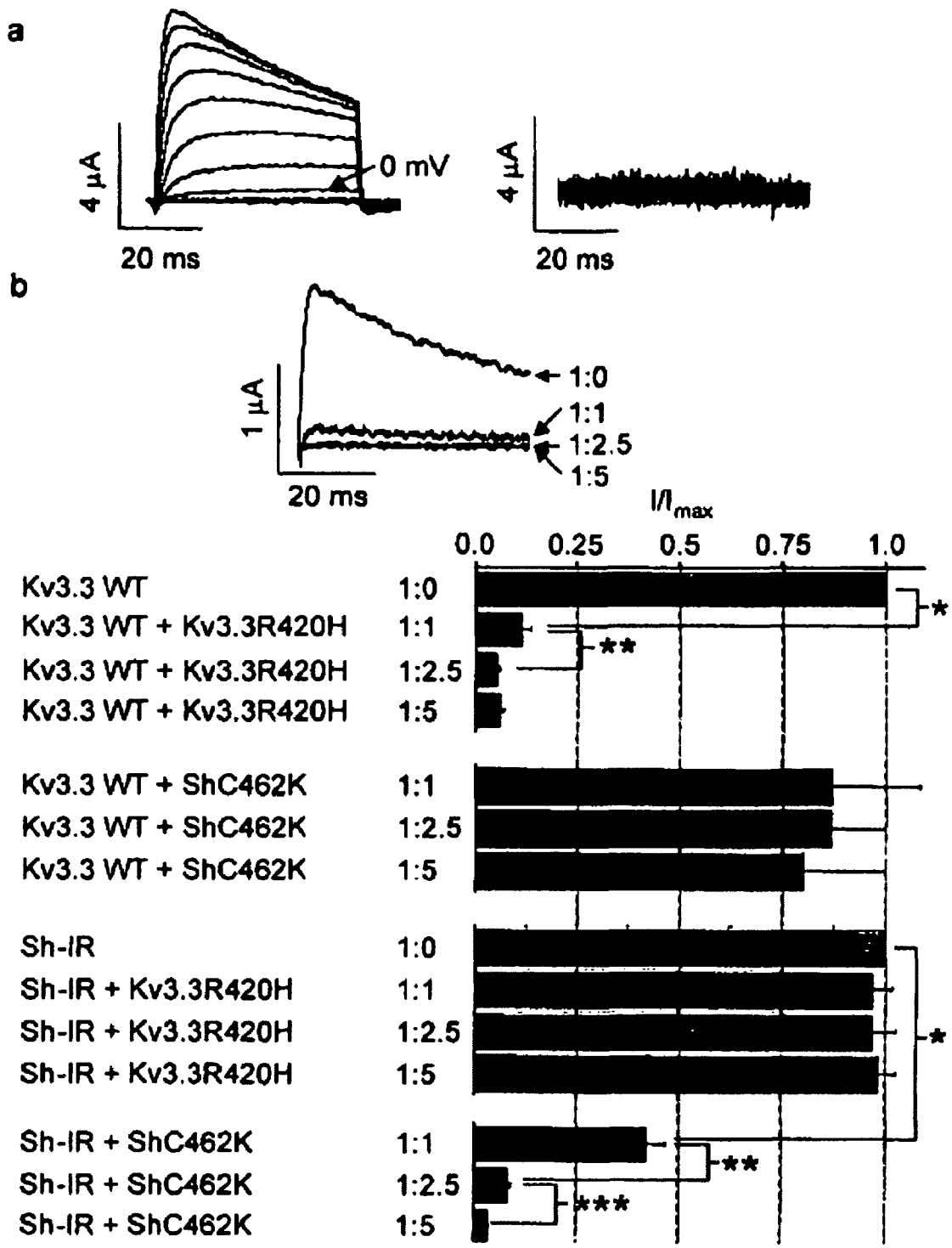
FIGS. 6A and B: Subfamily-specific dominant negative effect of R420H. a, Current traces from wildtype (left) and R420H (right) channels were evoked by stepping from −90 mV to voltages ranging from −80 to +70 mV in 10 mV increments. In wildtype, partial inactivation was observed at potentials greater than +20 mV. The 0 mV record from wildtype channels is labeled for comparison to FIG. 4a. b, Upper panel shows representative current traces evoked by stepping from −90 mV to +60 mV for wildtype Kv3.3 expressed alone (1:0) or in the presence of R420H at the indicated ratios. Lower panel plots normalized peak current amplitudes at +60 mV for Kv3.3 wildtype expressed alone (1:0), or expressed with Kv3.3-R420H or Shaker-C462K (Sh-C462K, a non-functional Shaker subunit24) at the indicated ratios. Also shown are peak current amplitudes at +60 mV for inactivation-removed Shaker (Sh-IR) expressed alone (1:0), or expressed with Kv3.3-R420H or Sh-C462K at the indicated ratios. Values are provided as mean.±.SEM, n=4-10. Statistical significance tested by one way ANOVA, $p<0.05$: *, different from 1:0; , different from 1:1; *, different from 1:2.5.

"Shal, Shab, and Shaw Express Independent K+ Current Systems," *Neuron* 7(5):763-773 (1991); Shieh, C. C., et al., "Role of Transmembrane Segment S5 on Gating of Voltage-Dependent K+ Channels," *J. Gen. Physiol.* 109:767-778 (1997), the entire content of each is incorporated herein by reference). The depolarized voltage dependence and rapid deactivation that are characteristic of Kv3 channels are related properties conferred by specific amino acid residues in the voltage sensor and S5 (Covarrubias, M., et al. "Shal, Shab, and Shaw Express Independent K+ Current Systems," *Neuron* 7(5):763-773 (1991); Smith-Maxwell, C. J., et al., "Uncharged S4 Residues and Cooperativity in Voltage-Dependent Potassium Channel Activation," *J. Gen. Physiol.* 111:421-439 (1998), the entire content of each is incorporated herein by reference). Importantly, KCNC3 protein sequences in S4 and S5 are 100% conserved amongst phyla, suggesting strong selection for the specialized role of these channels (FIG. 5b). Consistent with this observation, screening over four hundred alleles from normal individuals of Filipino or Anglo-European descent revealed no polymorphisms at either site. To investigate the functional consequences of the SCA13 mutations, wildtype and mutant KCNC3 alleles were expressed in Xenopus laevis oocytes and channel activity was recorded using a two electrode voltage clamp. Activation of the wild type Kv3.3 channel was detected at −10 mV and more positive potentials (FIG. 6a). Upon repolarization to −90 mV, the channel closed quickly. In contrast, expression of R420H resulted in no detectable channel activity (FIG. 6a). Co-expression of wildtype Kv3.3 and R420H subunits led to suppression of current amplitude consistent with a dominant negative effect (FIG. 6b). R420H did not suppress the expression of Shaker, a member of the Kv1 family (FIG. 6b). These results indicated that Kv3 subfamily-specific co-assembly of wildtype and mutant subunits produced non-functional channels.

Figure 7:
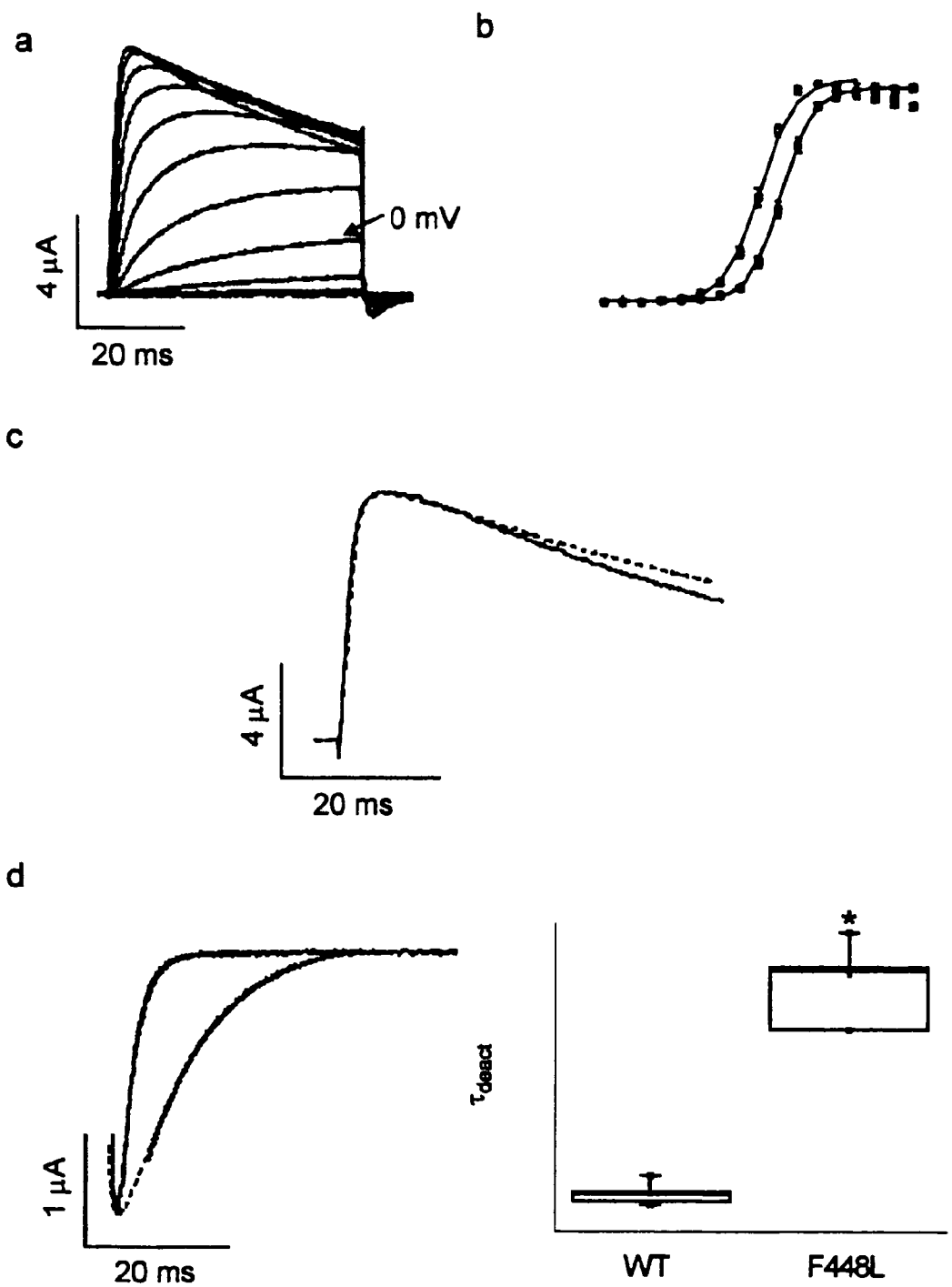
FIGS. 7A-D: Altered gating in F448L. a, Current traces from F448L channels were evoked by stepping from −90 mV to voltages ranging from −80 to +70 mV in 10 mV increments. The 0 mV record is labeled for comparison to FIG. 3a. b, To determine the probability of opening (Po) as a function of voltage, wildtype or F448L currents were evoked by stepping from −90 mV to various test potentials, followed by repolarization to −90 mV. The bath solution contained 89 mM Rb+. Isochronal tail current amplitudes were normalized to the maximal value obtained in the experiment and plotted versus test potential. Wildtype, filled squares; F448L, open squares. Values are provided as mean±SEM, n=6 (F448L) or 7 (wild-type). The data sets were fitted with single Boltzmann functions (solid lines), which yielded midpoint voltages of 2.8±1.0 mV and −9.6±1.3 mV and slope factors of 7.6±0.3 and 7.6±0.1 for wildtype and F448L channels, respectively. Midpoint voltages were significantly different, $p<0.05$ by one way ANOVA. c, Representative current traces obtained at +60 mV have been scaled and overlaid for wildtype (solid) and F448L (dashed). d, Left panel: Representative tail currents from wildtype (solid) and F448L (dashed), recorded in an 89 mM Rb+ bath solution, were obtained by stepping from +20 to −90 mV. The traces have been scaled and overlaid. Tail currents were fitted with a single exponential function (solid lines) to obtain values for the deactivation time constant, τdeact. Right panel: Box plot of τdeact for wildtype and F448L. Mean values±SEM were 2±0.2 ms and 13.3±1.0 for wildtype (n=7) and F448L (n=4), respectively. Values of τdeact differed significantly by one way ANOVA: *, $p<0.05$.

Expression of F448L produced channels with altered gating. Activation of F448L was detected at −20 mV, compared to −10 mV for wildtype (FIG. 7a). Analysis of the probability of opening as a function of voltage confirmed that activation was shifted ~13 mV toward the hyperpolarized direction (FIG. 7b). Activation kinetics of F448L and wildtype were similar at voltages where both have a maximal open probability (FIG. 7c). However, deactivation kinetics of F448L were dramatically slower. Tail currents were recorded after repolarization to −90 mV using an 89 mM Rb+ bath solution, and fitted with a single exponential component (FIG. 7d). This revealed a ~7-fold slowing of channel closure in F448L. The hyperpolarized shift in the probability of opening and the slower rate of deactivation are related findings indicating that F448L increases the relative stability of the open state. F448L makes the properties of Kv3.3 channels more similar to those of Shaker and other channels that normally have a leucine residue in the analogous position.

Unlike other SCA genes implicated in neurodegeneration, the physiological functions of Kv3 channels in the cerebellum have been extensively studied and are reasonably well understood (Seoh, S. A., et al., "Voltage-Sensing Residues in the S2 and S4 Segments of the Shaker K+ Channel," *Neuron* 16(6):1159-1167 (1996); Martina, M., et al., "Properties and Functional Role of Voltage-Dependent Potassium Channels in Dendrites of Rat Cerebellar Purkinje Neurons," *J. Neurosci.* 23(13):5698-5707 (2003); McKay, B. E. and Turner, R. W., "Kv3 K+ Channels Enable Burst Output in Rat Cerebellar Purkinje Cells," *Eur. J. Neurosci.* 20(3):729-739 (2004), the entire content of each is incorporated herein by reference). Kv3.3 is expressed in cerebellar granule cells, Purkinje cells, and deep cerebellar neurons, where it may form heteromultimeric channels by co-assembly with Kv3.1 and/or Kv3.4 (McKay, B. E. and Turner, R. W., "Kv3 K+ Channels Enable Burst Output in Rat Cerebellar Purkinje Cells," *Eur. J. Neurosci.* 20(3):729-739 (2004); Goldman-Wohl, D. S., et al., "Kv3.3b: A Novel Shaw Type Potassium Channel Expressed in Terminally Differentiated Cerebellar Purkinje Cells and Deep Cerebellar Nuclei," *J. Neurosci.* 14(2):511-522 (1994); Weiser, M. et al., "Differential Expression of Shaw-Related K+ Channels in the Rat Central Nervous System," *J. Neurosci.* 14(3):949-972 (1994), the entire content of each is incorporated herein by reference). In Purkinje cells, Kv3 channels are involved in repolarizing both somatic $Na^+$ spikes and dendritic $Ca^{3+}$ spikes (Martina, M., et al., "Properties and Functional Role of Voltage-Dependent Potassium Channels in Dendrites of Rat Cerebellar Purkinje Neurons," *J. Neurosci.* 23(13):5698-5707 (2003), the entire content of which is incorporated herein by reference). Kv3 channels are essential for fast spiking in neurons that fire hundreds of action potentials per second with little or no frequency adaptation (Ghanshani, S. et al., "Genomic Organization, Nucleotide Sequence, and Cellular Distribution of a Shaw-Related Potassium Channel Gene, Kv3.3, and Mapping of Kv3.3 and Kv3.4 to Human Chromosomes 19 and 1," *Genomics* 12(2):190-196 (1992), the entire content of which is incorporated herein by reference). Because of their depolarized activation range, Kv3 channels open only during action potentials, contribute to fast repolarization, and thus promote recovery of $Na^+$ channels from inactivation. Fast deactivation of Kv3 channels limits the time course of the after-hyperpolarization, thereby shortening the refractory period.

In all likelihood, the SCA13 mutations disrupt the firing properties of fast spiking cerebellar neurons. Although the Kv3.3 knock-out mouse has no obvious motor phenotype, the double Kv3.1/Kv3.3 knock-out has dramatic symptoms, including tremor and severe ataxia (Smith-Maxwell, C. J., et al., "Uncharged S4 Residues and Cooperativity in Voltage-Dependent Potassium Channel Activation," *J. Gen. Physiol.* 111:421-439 (1998), the entire content of which is incorporated herein by reference). Because R420H is expected to suppress the functional expression of Kv3.3 as well as other subunits in the Kv3 family, this mutation may be more comparable to the double knockout. Pharmacological suppression of Kv3 activity in cerebellar neurons leads to action potential broadening, spike frequency adaptation, and spike failure from accumulated $Na^+$ channel inactivation (Martina, M., et al., "Properties and Functional Role of Voltage-Dependent Potassium Channels in Dendrites of Rat Cerebellar Purkinje Neurons," *J. Neurosci.* 23(13):5698-5707 (2003), the entire content of which is incorporated herein by reference). R420H may have a similar effect. In contrast, F448L is predicted to reduce the maximal firing rate of cerebellar neurons. Due to slower closing, after-hyperpolarization would be prolonged thus delaying the return to threshold and increasing the interspike interval. The differing effects of the mutations at the cellular level are consistent with the contrasting phenotypes in the two pedigrees. Whereas R420H reduces current amplitude with no change in channel properties, F448L alters key parameters of gating. The more severe functional alterations of the F448L are consistent with the earlier onset and more static disease course observed in the French pedigree.

The physiological properties of Kv3 channels provide tantalizing clues for potential mechanisms of neurodegeneration. Kv3 channels contribute significantly to the repolarization of dendritic $Ca^{2+}$ spikes in Purkinje cells (Martina, M., et al., "Properties and Functional Role of Voltage-Dependent Potassium Channels in Dendrites of Rat Cerebellar Purkinje Neurons," *J. Neurosci.* 23(13):5698-5707 (2003), the entire content of which is incorporated herein by reference). Longer duration spikes would increase $Ca^{2+}$ influx, which may contribute to neuronal death. Additionally, the functional properties of Kv3.3 and Kv3.4 channels are modulated by reactive oxygen species (Weiser, M. et al., "Differential Expression of Shaw-Related K+ Channels in the Rat Central Nervous System," *J. Neurosci.* 14(3):949-972 (1994); Espinosa, F., et al., "Alcohol Hypersensitivity, Increased Locomotion, and Spontaneous Myoclonus in Mice Lacking the Potassium Channels Kv3.1 and Kv3.3," *J. Neurosci.* 21(17):6657-6665 (2001); Ruppersberg, J. P. et al., "Regulation of Fast Inactivation of Cloned Mammalian IK(A) Channels by Cysteine Oxidation," *Nature* 352(6337):711-714 (1991); Vega-Saenz de Miera, E. and Rudy, B., "Modulation of K+ Channels by Hydrogen Peroxide," *Biochem. Biophys. Res. Comm.* 186(3):1681-1687 (1992); Duprat, F., "Susceptibility of Cloned K+ Channels to Reactive Oxygen Species," *Proc. Natl. Acad. Sci. U.S.A.* 92(25):11796-11800 (1995), the entire content of each is incorporated herein by reference). Mutant Kv3.3 subunits may affect the ability of cerebellar neurons to cope with oxidative stress. Finally, morphological differentiation and the development of hallmark electrical properties are tightly linked in Purkinje cells. This raises the possibility that morphological and electrical maturation are interdependent phenomena (Vega-Saenz de Miera, E. and Rudy, B., "Modulation of K+ Channels by Hydrogen Peroxide," *Biochem. Biophys. Res. Comm.* 186(3):1681-1687 (1992), the entire content of which is incorporated herein by reference; McKay, B. E., and Turner, R. W., "Physiological and Morphological Development of the Rat Cerebellar Purkinje Cell," *J. Physiol.* 567(3): 829-850 (2005), the entire content of each is incorporated herein by reference). Mutations that disrupt acquisition of appropriate electrical characteristics may cause subtle developmental defects that reduce the long-term viability of the neurons.

The results point to voltage-gated potassium channels as valid candidates for genes involved in phenotypes ranging from developmental disorders to late-onset neurodegenerative disease. It is likely that in vivo systems will be required to assess the consequences of mutant KCNC3 on three distinct but interrelated functions: cerebellar development, cerebellar function in the mature organism and the role of proper channel function preventing neuronal death. Both mutations show some intra-familial phenotypic variability highlighting the importance of compensatory mechanisms and the likely presence of other genetic and environmental modifiers. Further understanding of the role of voltage-gated K channels in cerebellar degeneration may lead to therapies aimed at modulating channel function not only to restore cerebellar function but also to reduce neurodegeneration.

Although abnormalities of ion channels are rare causes of diseases of the heart, kidney, and skeletal muscle (Long, S. B., et al., "Crystal Structure of a Mammalian Voltage-Dependent Shaker Family K+ Channel," *Science* 309(5736):897-903 (2005); Shieh, C. C., et al., "Role of Transmembrane Segment S5 on Gating of Voltage-Dependent K+ Channels," *J. Gen. Physiol.* 109:767-778 (1997); Graves, T. D. and Hanna, M. G., "Neurological Channelopathies," *Postgrad. Med. J.* 81(951):20-32 (2005); Dworakowska B. and Dolowy, K., "Ion Channels-Related Diseases," *Acta Bioch. Pol.* 47(3): 685-703 (2000), the entire content of each is incorporated herein by reference), KCNC3 was not a likely candidate for a degenerative ataxia, as potassium channel mutations are not associated with neurodegeneration, but with episodic phenomena such as epilepsy and episodic ataxia. Furthermore, KCNC3 deficiency in the mouse did not produce a phenotype (Smith-Maxwell, C. J., et al., "Uncharged S4 Residues and Cooperativity in Voltage-Dependent Potassium Channel Activation," *J. Gen. Physiol.* 111:421-439 (1998); Espinosa, F., et al., "Alcohol Hypersensitivity, Increased Locomotion, and Spontaneous Myoclonus in Mice Lacking the Potassium Channels Kv3.1 and Kv3.3," *J. Neurosci.* 21(17):6657-6665 (2001), the entire content of each is incorporated herein by reference).

Potassium channels are ubiquitous in nature and play significant roles in nerve and muscle tissue electrical excitability in mammals. Potassium channelopathies are known to cause episodic neurological diseases in humans. The present invention has identified mutations in the voltage-gated potassium channel, KCNC3 (Kv3.3), which cause the neurodevelopmental/degenerative disorder SCA13. One mutation, located in the voltage-sensing domain, causes a dominant negative effect. A second mutation, located in the domain effecting voltage-sensor conformational changes conferring pore opening and closing, shifts the activation curve more negative and slows channel closing. This characterization expands the role of potassium channels in neurological diseases and suggests their importance in both neurodevelopment and neurodegeneration.

Potassium channels influence many aspects of electrical excitability in nerve and muscle, and mutations in their genes have been described in episodic neurological diseases (Graves, T. D. and Hanna, M. G., "Neurological Channelopathies," *Postgrad. Med. J.* 81(951):20-32 (2005); Dworakowska B. and Dolowy, K., "Ion Channels-Related Diseases," *Acta Bioch. Pol.* 47(3):685-703 (2000); Mulley, J. C. et al., "Channelopathies as a Genetic Cause of Epilepsy," *Curr. Opin. Neurol.* 16(2):171-176 (2003), the entire content of each is incorporated herein by reference). The present invention now demonstrates that $K^+$ channel mutations also cause a neurodevelopmental/degenerative disease, spinocerebellar ataxia. In a Filipino pedigree with adult-onset ataxia, the causative gene maps to 19g13, overlapping the SCA 13 locus previously described in a French pedigree with childhood-onset mental retardation, ataxia and seizures (Herman-Bert, A., et al., "Mapping of Spinocerebellar Ataxia 13 to Chromosome 19q13.3-q13.4 in a Family with Autosomal Dominant Cerebellar Ataxia and Mental Retardation," *Am J Hum Genet* 67(1):229-235 (2000), the entire content of which is incorporated herein by reference). This region contains KCNC3 (Kv3.3), which encodes a voltage-gated Shaw potassium channel with enriched cerebellar expressions. Sequencing KCNC3 revealed mutations 1554G→A (R420H) in the Filipino and 1639C→A (F448L) in the French pedigrees. Both mutations alter KCNC3 function in the Xenopus oocyte expression system. KCNC3 R420H, located in the voltage sensor of the channel (Aggarwal, S. K. and MacKinnon, R., "Contribution of the S4 Segment to Gating Charge in the Shaker K+ Channel," *Neuron* 16(6):1169-1177 (1996), the entire content of which is incorporated herein by reference), has no detectable channel activity when expressed alone and a strong dominant negative effect when co-expressed with wildtype KCNC3. KCNC3 F448L shifts the activation curve in the negative direction and slows channel closing by ~7-fold. Thus, R420H and F448L mutations are expected to change the output characteristics of fast-spiking cerebellar neurons, where KCNC channels confer capacity for high frequency firing. The present invention has identified voltage-gated potassium channels as valid candidates for genes involved in phenotypes ranging from developmental disorders to adult-onset neurodegeneration.

EXAMPLE 3

Analysis of European Pedigrees With Autosomal Dominant Ataxia of Early or Late Onset Methods:

Identification of Index Cases:

The study group was composed of 260 index cases from European autosomal dominant ataxia families. All patients underwent clinical examinations and genetic tests to exclude SCA1, 2, 3, 6, 7 and 17.

The control group included 244 alleles contributed by 77 normal individuals living in France and 55 United States individuals that represented spouses of patients with Parkinson disease.

Mutation Detection:

For mutation screening intronic and exonic PCR primer pairs were designed from genomic sequence to amplify each exon of the KCNC3 gene, including the flanking splice sites with a set of 5 PCR primer pairs. Due to the complexity in the amplification of exon 1 three different primer pairs overlapping at least 100 base pairs were designed to amplify the entire exon. Exon 2 was amplified utilizing one primer pair composed of a total of 1330 base pairs and Exon 3 and 4 were amplified as one amplicon with primer pairs flanking each exon respectively encompassing the entire intron 3. These PCR reactions were done under the following conditions: 50 ng (5 ul) of genomic DNA, 1× (2 ul) of 10× Buffer (Qiagen), 1 unit (0.2 ul) of Hot Taq (Qiagen), 2 ul of Q solution (Qiagen) and dd H20 up to 20 ul. The PCR cocktails were amplified as follows: Exon 1 (all 3 amplicons) and Exon 3-4 used an initial denaturation of 94° C. for 15 minutes, followed by 10 cycles at 95° C. 1 minute 10 seconds, 67° C. 30 seconds, 72° C. 1 minute 30 seconds followed by 30 cycles of 95° C. 1 minute 10 seconds, 65° C. 30 seconds, 72° C. 1 minute 30 seconds followed by an extension of 72° C. for 5 minutes. Exon 2 was amplified at 95° C. for 15 minutes, 35 cycles of 95° C. 1 minute, 60° C. 30 seconds, 72° C. 2 minutes with a final extension of 72° C. 7 minutes.

PCR products were checked on agarose gels, and then sequenced as detailed below. Each fragment containing mutations was PCR amplified and sequenced a second time on new DNA aliquots to confirm that the identified mutations were not due to PCR artifact.

Sequence Analysis:

DNA sequencing was performed using the ABI BigDye Terminator v3.1 cycle sequencing kit and the following protocol: 10 ng (2 ul) of purified PCR amplicon, 3 ul sequencing reaction pre-mix, 2 ul 5× sequencing buffer, 80 ng (2 ul) of primer and 11 ul of DD $H_2O$. PCR primers and conditions are shown in Table 1. The reaction mix was run in a PCR thermocycler (Bio-Rad MyCycler v 1.065) and cycled as follows: 96° C. for 3 minutes followed by 25 cycles consisting of 96° C. for 10 seconds, 50 for 5 seconds and 60° C. for 4 minutes. Sequencing products were purified using ABI Centri-Sep spin columns. Resuspended samples were electropheresed on an ABI 377 DNA sequencer. All sequences were analyzed using BioEdit biological sequence alignment editor (v5.0.9.1, Tom Hall, Isis Pharmaceuticals).

Analysis of Channel Function:

Mutations were introduced into the human wildtype Kv3.3 clone (using the QuikChange kit 9Stratagene) (Rae, J. L., and Shepard, A. R., "Kv3.3 Potassium Channels in Lens Epithelium and Corneal Endothelium," Exp. Eye. Res. 70(3):339-348 (2000), the entire content of which is incorporated herein by reference).

Mutations were verified by sequencing. Run off transcripts were prepared in vitro using the mMessage mMachine kit (Ambion). Wild type and mutant subunits were expressed alone or in carefully controlled ratios by injecting RNA into Xenopus oocytes. Channel activity was recorded 2-3 days later using a two electrode voltage clamp (Papazian, D. M. et al., "Alteration of Voltage-Dependence of Shaker Potassium Channel by Mutations in the S4 Sequence," Nature 349(6307):305-310 (1991), the entire content of which is incorporated herein by reference). During electrophysiological experiments, oocytes were bathed in a solution containing 4 mM KCL, 85 mM NaCl, 1.8 mM CaCl2, and 10 mM HEPES, pH 7.2. Electrode resistances ranged from 0.3 to 0.8 MΩ.

Results:

Genetics:

KCNC3 is composed of 5 exons encompassing a 13,870 kb region in chromosome 19; the mRNA is 3176 bp of which 2274 bp are coding. The entire coding region for DNA variants in 260 index cases of European descent with autosomal dominant ataxia was screened. The index cases were from families with late as well as early disease onset.

Table 2 shows the DNA sequence changes found in 260 index cases and 122 controls. All variants were present in the heterozygous state. Exon 5 was not analyzed as it did not contain any coding sequences. A total of 14 variants were identified. These consisted of 13 single nucleotide polymorphisms (SNPs), and one 9 bp insertion. Seven variants were located in the coding region, and four resulted in amino acid changes. The 9 bp insertion resulted in the addition of 3 amino acids in exon 1 and was observed in 1 control. There were 3 SNPs that resulted in amino acid changes. All three changed an arginine to a histidine (R366H, R420H, and R423H) and were observed in cases, but not in controls. The corresponding single nucleotide polymorphisms (SNPs) were a substitution of guanine with adenine as follows: 1554G→A (R420H), 1563G→A (R423H), and 1392G→A (R366H).

A number of variants, which did not change the predicted amino acid sequence, were identified either in the 5-UTR, or as synonymous changes in exons 1 or 2. These variants each occurred at a frequency of <1% in either cases or controls and

TABLE 1

| Exon | Seq. ID No. | Primer Sequence 5' to 3' | Prime Name | Size | Annealing Temp |
|---|---|---|---|---|---|
| 1 | SEQ ID NO: 1 | TAG GTG AGG GCG TGG GAT CTG TT | 1A-F | 584 | 64'C |
| | SEQ ID NO: 48 | GCC CGC GAA AGG ACG AGA C | 1A-R | | |
| 1 | SEQ ID NO: 3 | CTC CCA CCC AAT CCC GTC GGT C | 1B-F | 658 | 64'C |
| | SEQ ID NO: 4 | GCG ATG CTG CCG GTA GGT CAT CC | 1B-R | | |
| 1 | SEQ ID NO: 5 | TTC GCG TAC GTG CTC AAC TAC TA | 1C-F | 583 | 64'C |
| | SEQ ID NO: 6 | TGG GGA AGA GGC TTC TAG GAG | 1C-R | | |
| 2 | SEQ ID NO: 32 | CTG GAA GGG TCT TCT GGA TGT TA | 2A-F | 1330 | 60'C |
| | SEQ ID NO: 47 | TTT TCT CCC TCA CCT CTT CGA C | 2A-R | | |
| 3/4 | SEQ ID NO: 11 | ATC TTG CCC CAC CGC GTG TTC A | 3-4-F | 779 | 64'C |
| | SEQ ID NO: 12 | CGG TCA GTG GGG GCT GCA TGT TC | 3-4-R | | | likely represent rare normal alleles. Subtle effects on channel abundance, however, cannot be excluded at this time. No variants were detected in exons 3 and 4 or within 10 bp of exon/intron junctions.

Other than exon-intron boundaries, the introns were not sequenced with the exception of intron 3, which was sequenced due to its small size. DNA variants were most common in intron 3. Four SNPs were detected. One SNP, located at position 73 in intron 3 (rs9917109), was relatively common and found in 7.5% of cases (3.25% of alleles), but only in 0.82% of controls. Population frequencies for SNP rs9917109 have not been reported. The significance of this finding is unknown as the study was not designed to examine differences in frequencies of variants found in cases and controls. The biologic consequences of variants seen in cases, but not controls, remain unknown at this time. Even though functional effects cannot be immediately gleaned from the sequence changes, it is possible that these variants could contribute to development or progression of disease.

A total of 6 index cases with variants in the coding region that resulted in changes of the amino acid sequence were found. These variants were not detected in normal control samples (Table 2). The clinical phenotypes are shown in Table 3. The variants identified were R420H, R423H and R366H mutations and are discussed in detail below.

TABLE 2

| Location | Variant | Type | SEQ ID NO: | Flanking Sequence | Amino Acid Change | % cases | % controls |
|---|---|---|---|---|---|---|---|
| 5' UTR −297 bp from A of first ATG | T/C | Non-coding | SEQ ID NO: 33 | GGTCTCT/CCTCTAT | | 0.38 | 0 |
| 5' UTR −403 bp from A of first ATG | C/T | Non-coding | SEQ ID NO: 34 | TCCCCTC/TCTCCCT | | 0.38 | 0 |
| 5' UTR −415 bp from A of first ATG | T/G | Non-coding | SEQ ID NO: 35 | CGTCTTT/GAAATAG | | 0.77 | 0 |
| Exon 1 | C/T | Synonymous | SEQ ID NO: 36 | AGTCTGC/TGTCTCG | C6C | 0.38 | 0 |
| Exon 1 | 9 bp insert | Coding | SEQ ID NO: 37 | AAC/GCCGCCAAC/GCC | 218AAN | 0 | 0.82 |
| Exon 2 | C/T | Synonymous | SEQ ID NO: 38 | CACCAAC/TGAGTTC | N339N | 0.38 | 0 |
| Exon 2 | G/A | Coding | SEQ ID NO: 39 | TCATGCG/ACATCAC | R366H | 0.38 | 0 |
| Exon 2 | G/A | Coding | SEQ ID NO: 40 | TCGTCCG/ACATCCT | R420H | 1.15 | 0 |
| Exon 2 | G/A | Coding | SEQ ID NO: 41 | TCCTGCG/ACATCTT | R423H | 0.77 | 0 |
| Exon 2 | G/A | Synonymous | SEQ ID NO: 42 | CTACGTG/AGAGGGG | V351V | 0.38 | 0 |
| Intron 3 +14 bp | C/A | Non-coding | SEQ ID NO: 43 | GCCCCCC/ACTACTG | | 1.15 | 0.82 |

TABLE 2-continued

| Location | Variant | Type | SEQ ID NO: Flanking Sequence | Amino Acid Change | % cases | % controls |
|---|---|---|---|---|---|---|
| Intron 3 +70 bp | G/A | Non-coding | SEQ ID NO: 44 AGGAGAG/AGGGGAT | | 0.38 | 0 |
| Intron 3 +73 bp | G/A | Non-coding | SEQ ID NO: 45 AGAGGGG/AGATGGG | | 7.31 | 0.82 |
| Intron 3 +215 bp | T/C | Non-coding | SEQ ID NO: 46 CCCAACT/CCTCTGG | | 0.77 | 0 |

TABLE 3

| Mutation | Family ID | Index Patient | Age at On-set | Age at Exam (y) | Sign at on-set | Cerebellar signs | LL Pyramidal signs | Mental Retardation | Imaging | Seizures | Progression |
|---|---|---|---|---|---|---|---|---|---|---|---|
| R420H | MR 164-3 | Yes | >25 | 43 | Ataxic gait | Yes | No | No | CCA | No | Yes |
| R420H | MR-3-1 | Yes | 42 | 66 | Ataxic gait and seizures | Yes | Yes | No | CCA | No | Yes |
| R420H | MR-3-3 | No | 28 | 31 | Ataxic gait | Yes | Yes | No | CCA | Yes | Yes |
| R420H | BOR-542-3 | Yes | 51 | 57 | Ataxic gait | Yes | Yes | No | Vermian atrophy WM changes | No | NA |
| R423H | SAL-289-6 | Yes | infancy | 47 | Motor delay with ataxia gait, falls, dysarthria, writing difficulties | Yes | No | No | NA | No | Stable |
| R423H | AAD-SAL-289-12 | No | 2 | 17 | Motor delay with ataxic gait and falls | Yes | No | No | normal (age 3) | No | Stable |
| R423H | STR-198-14 | Yes | infancy | 3 | Ataxia | Yes | No | No | NA | No | NA |
| R423H | STR-198-10 | No | 3 | 33 | Motor delay with ataxic gait, dysarthria | Yes | Yes | No | NA | No | Stable |
| R366H | BOR-352-6 | Yes | 63 | 63 | ataxia | Yes | No | | | | Yes |

In regard to the R420H mutation, three European index cases with the R420H mutation were identified. This mutation was previously identified in a Filipino pedigree (Waters, M. F., et al., "Mutations in the Voltage-Gated Potassium Channel KCNC3 Cause Degenerative and Developmental CNS Phenotypes," *Nat Genet.* 38(4):447-451 (2006), the entire content of which is incorporated herein by reference). Two of these originated from Germany and one from France. All individuals with the R420H mutation shared adult onset, predominantly cerebellar signs, and slowly progressive course. Neuroimaging confirmed cerebellar atrophy. Age of onset ranged from 25 to 61. Imaging showed cerebellar atrophy in all cases. One individual (TUB 3-3), daughter of a male index case, had a disease onset at age 28 with an ataxic gait, and also developed seizures. These seizures emanated from a temporal lobe focus, and the patient is currently being evaluated for epilepsy surgery. In contrast to other individuals with the R420H mutation, this father-daughter pair also exhibited lower leg spasticity.

A novel R423H mutation in two index cases was also identified. Similar to the F448L mutation previously described in a large French family, these individuals had an early onset, but in contrast did not exhibit mental retardation or seizures. Age at onset was described as being in infancy and detected as delay in acquisition of motor milestones. One individual had a computerized tomography scan at age 3 with normal results and one cerebellar atrophy on cerebral MRI. Four individuals were examined at ages 12, 17, 33, and 47 and had had little progression of disease with regard to gait ataxia and dysarthria. Seizures were not reported in these individuals, but one individual had lower leg spasticity and one increased reflexes in the lower limbs.

R423 is one of several arginine residues in the S4 transmembrane segment that sense and respond to changes in voltage (Aggarwal, S. K. and MacKinnon, R., "Contribution of the S4 Segment to Gating Charge in the Shaker K+ Channel," *Neuron* 16(6):1169-1177 (1996); Seoh, S. A., et al., "Voltage-Sensing Residues in the S2 and S4 Segments of the Shaker K+ Channel," *Neuron* 16(6):1159-1167 (1996), the entire content of which is incorporated herein by reference). The positively charged residues in S4, including R420 and R423, are responsible for voltage-dependent conformational changes that result in channel opening or closing. This novel mutation had strong dominant-negative characteristics similar to R420H.

A novel R366H mutation in the heterozygous state was also found in the intracellular end of the S2 transmembrane segment in the voltage gated sensor domain and was seen in one male index case with an age of ataxia onset at 65. The amino acid sequence of the S2 domain is shown in SEQ ID NO: 49 and the nucleotide sequence is shown in SEQ ID NO: 50. His affected nephew with an age of onset at 45 did not carry this change. The nephew's father was unaffected. This family was lost to follow-up and no imaging findings were available. A brother of the index case had a rapidly progressive disease with ataxia and speech problems just prior to death. This patient was negative for the R366H mutation as well as for a PRN mutation, but tested positive for the 14-3-3 protein by western blot analysis (data not shown).

Functional Analysis:

To characterize the effects of the newly-identified mutations on channel function, the R423H mutation and the R366H variant were generated in wild type human Kv3.3 (Rae, J. L., and Shepard, A. R., "Kv3.3 Potassium Channels in Lens Epithelium and Corneal Endothelium," *Exp. Eye. Res.* 70(3):339-348 (2000). the entire content of which is incorporated herein by reference). Wild type and mutant subunits were expressed in Xenopus oocytes and channel activity was recorded with a two electrode voltage clamp (Papazian, D. M. et al., "Alteration of Voltage-Dependence of Shaker Potassium Channel by Mutations in the S4 Sequence," *Nature* 349(6307):305-310 (1991), the entire content of which is incorporated herein by reference).

Figure 9A:
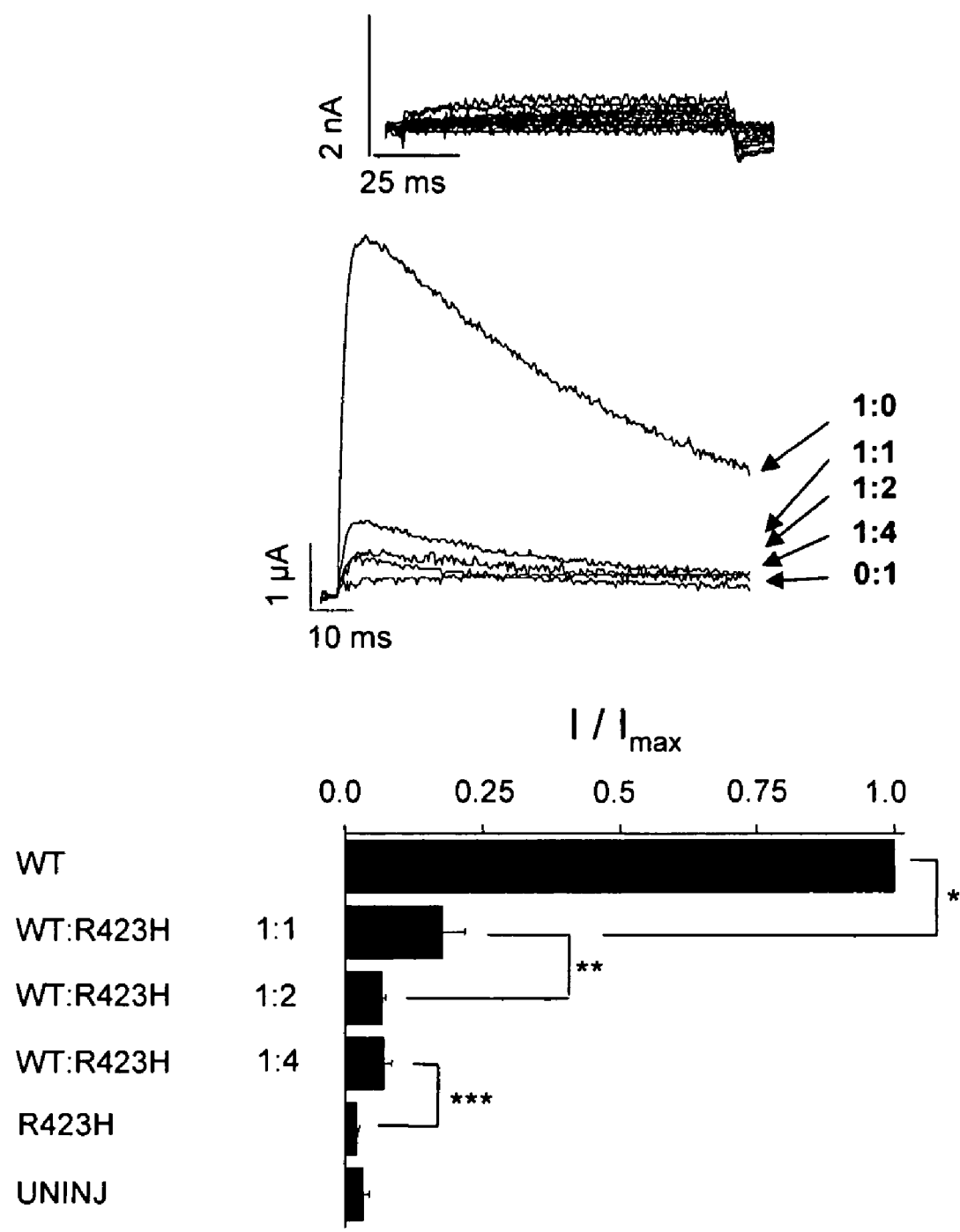
FIGS. 9A and B: Dominant negative effects of KCNC3 mutations. Top: R423H (A) or R366H (B) were expressed in Xenopus oocytes for functional analysis. Currents were evoked by stepping from −90 mV to voltages ranging from −80 to +70 mV in 10 mV increments. Middle: Shown are representative current traces evoked by stepping from −90 mV to +60 mV for wild-type Kv3.3 expressed alone or in the presence of R423H or R366H at the indicated ratios. Below: Normalized peak current amplitudes measured at +60 mV are shown for wild-type expressed alone or with R423H or R366H at the indicated ratios. For comparison, values for R423H or R366H expressed alone or from uninjected oocytes (Uninj) are also provided. Values are given as mean±SEM, n=4-10. Statistical significance was tested by one-way analysis of variance (ANOVA). P<0.05: *, significantly different from 1:0; , significantly different from 1:1, *, significantly different from 1:4.

The R423H mutant was non-functional when expressed alone (FIG. 9A, top). Upon co-expression with wild type, the R423H subunit suppressed activity consistent with a strong dominant negative effect (FIG. 9A, middle). At a 1:1 expression ratio of wild type and R423H, which is the expected ratio found in SCA13 patients, current amplitudes measured at +60 mV were ~20% of wild type expressed alone. Current amplitudes were further suppressed at ratios of 1:2 and 1:4 (wild type: R423H) (FIG. 9A, bottom).

In addition, despite the shared early-onset phenotype between F448L mutation and the R423H mutation, the effects of the two mutations in a heterologous expression system were distinct. The R423H mutation generated non-functional subunits with a strong dominant negative effect on channel expression, whereas the F448L mutation increased the stability of the open state of the channel. The previously reported F448L mutation (Waters, M. F. et al., "Mutations in the Voltage-Gated Potassium Channel KCNC3 Cause Degenerative and Developmental CNS Phenotypes," *Nat Genet.* 38(4):447-451 (2006), the entire content of which is incorporated herein by reference) remains the only KCNC3 mutations with a cellular gain-of-function phenotype.

Therefore, the initial notion that gain-of-function mutations in KCNC3 would be associated with early-onset and dominant-negative mutations with late-onset and progression is not supported. It is currently unknown why the two dominant-negative mutations, R420H and R423H, have such different phenotypes. It remains possible that R423H has gain of function effects that were not detected in these experiments. For instance, mutations in conserved S4 arginine residues of the Nav1.4 voltage-gated $Na^+$ channel associated with hypokalemic periodic paralysis-generate aberrant leak currents through putative 'gating pores' in the voltage sensor domain that may contribute to the disease phenotype (Sokolov, S. et al., "Gated Pore Current in an Inherited Ion Channelopathy," *Nature* 446(7131):76-78 (2007); Struyk, A. F. and Cannon, S. C. "A Na+ Channel Mutation Linked to Hypokalemic Periodic Paralysis Exposes a Proton-Selective Gating Pore," *J. Gen. Physiol.* 130(1):11-20 (2007); Struyk, A. F., et al., "Gating Pore Currents in DIIS4 Mutations of Nav1.4 Associated with Periodic Paralysis: Saturation of Ion Flux and Implications for Disease Pathogenesis," *J. Gen. Physiol.* 132(4):447-464 (2008), the entire content of each is incorporated herein by reference).

Figure 9B:
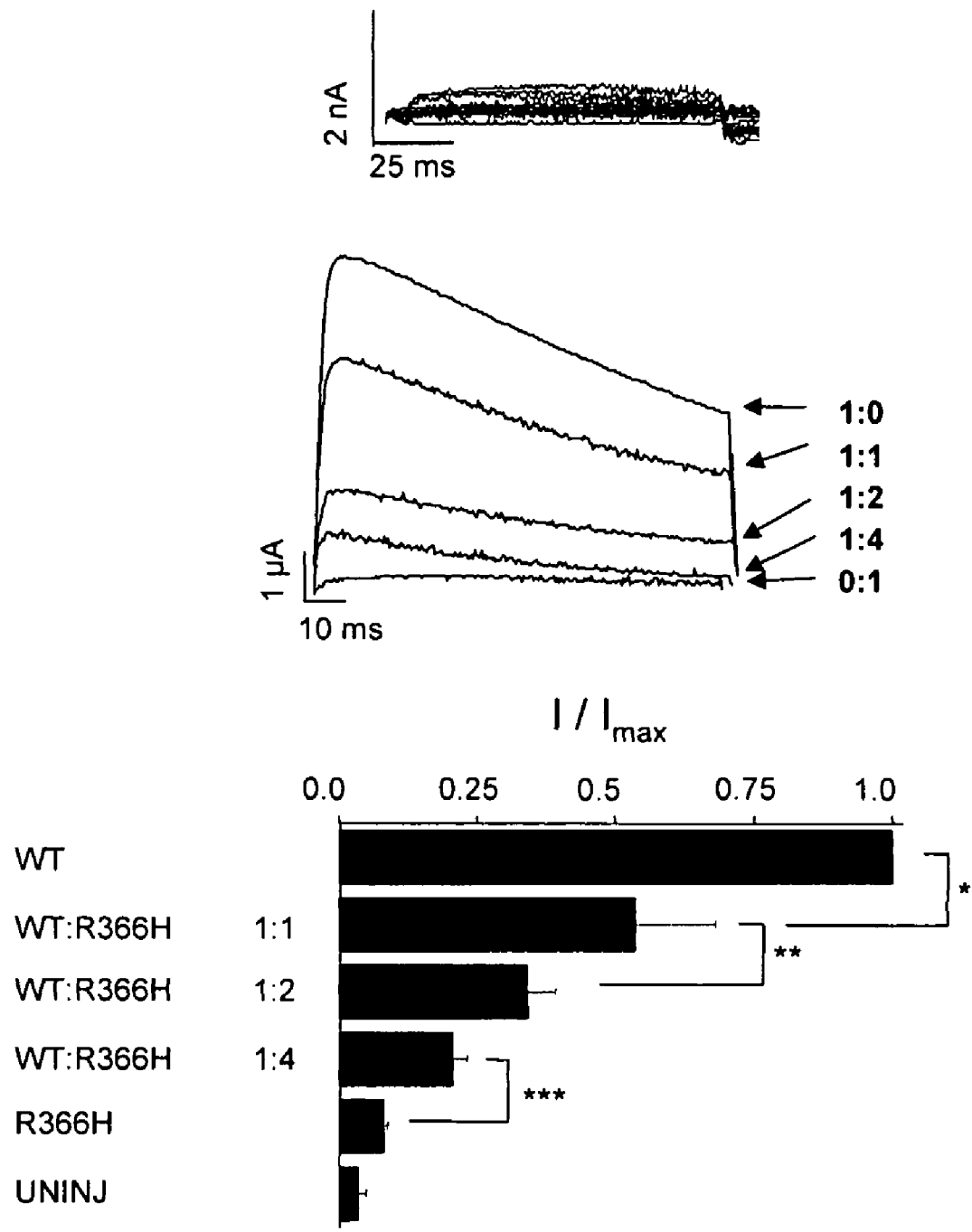

The R366H mutant was also non-functional when expressed alone (FIG. 9B, top). R366H subunits had a dominant negative effect on expression of wild type, although the level of suppression was less than that seen with R423H or the previously described R420H mutation (FIG. 9B, middle and bottom). At a 1:1 expression ratio of wild type and R366H, current amplitudes were ~50% of wild type expressed alone. Increasing the amount of the mutant subunit led to further decreases in current amplitude (FIG. 9B, bottom). This contrasts with virtual suppression of current amplitudes upon co expression of the R420H mutation. This variant did not segregate in the family, but the possibility remains that the affected nephew without the R366H change represents a phenocopy. Recently reported X-ray structures of voltage-gated potassium channels indicate that this positively-charged residue is involved in a network of electrostatic interactions that likely stabilizes the voltage sensor domain (Long, S. B., et al., "Crystal Structure of a Mammalian Voltage-Dependent Shaker Family K+ Channel," *Science* 309(5736):897-903 (2005); Long, S. B., et al. "Atomic Structure of a Voltage-Dependent K+ Channel in a Lipid Membrane-Like Environment," *Nature* 450(7168):376-382 (2007), the entire content of each is incorporated herein by reference)).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of diagnosing spinocerebellar ataxia 13 (SCA13) or predicting the risk of developing SCA13 in a human comprising:
   a) analyzing a nucleic acid sample obtained from the human for the presence or absence of a mutation in the transmembrane domain of the KCNC3 gene; and
   b) determining the presence or absence of a missense mutation in the nucleotide sequence of a transmembrane domain of the KCNC3 gene in the sample, wherein the missense mutation in the nucleotide sequence of the transmembrane domain results in a change in the output characteristics of fast spiking cerebellar neurons, whereby determining the presence of the missense mutation in the nucleotide sequence of the transmembrane domain is indicative that the individual has or is at risk of developing SCA13.

2. The method of claim 1, wherein the transmembrane domain is selected from the group consisting of the S4 and S5 transmembrane domain.

3. The method of claim 2, wherein the transmembrane domain is the S4 transmembrane domain, and wherein the nucleotide sequence of wild type S4 transmembrane domain encodes a wild type polypeptide comprising amino acid sequence SEQ ID NO: 20.

4. The method of claim 2, wherein the transmembrane domain is the S5 transmembrane domain, and wherein the nucleotide sequence of wild type S5 transmembrane domain encodes a wild type polypeptide-comprising amino acid sequence SEQ ID NO: 21.

5. The method of claim 1, wherein the mutation is detected by dot blot hybridization.

6. The method of claim 1, wherein the mutation is detected by southern blot hybridization.

7. The method of claim 1, wherein the nucleic acid sample is amplified and wherein said mutation is detected by sequencing said amplification product.

8. The method of claim 1, wherein the mutation causes an amino acid substitution in SEQ ID NO: 17 selected from the group consisting of R420H and F448L.

9. The method of claim 1, wherein the human has one or more of the following phenotypes selected from the group consisting of: epilepsy, mental retardation, cerebellar ataxia, extrapyramidal signs, dysarthria, oculomotor abnormalities, motor neuron signs, cognitive decline, autonomic dysfunction, sensory deficits and psychiatric manifestations.

10. The method of claim 1, wherein the mutation causes an amino acid substitution of R423H.

* * * * *

UNITED STATES PATENT AND TRADEMARK OFFICE
CERTIFICATE OF CORRECTION

PATENT NO.        : 8,163,483 B2
APPLICATION NO.   : 12/386427
DATED             : April 24, 2012
INVENTOR(S)       : Stefan M. Pulst Page 1 of 1

It is certified that error appears in the above-identified patent and that said Letters Patent is hereby corrected as shown below:

In the Specification

In Column 1, beginning at Line 14, and ending at Line 18, please delete:

"This invention was made with United States Government support under Grants No. R01GM43459, R01GM6686, R01N533123, T32GM065823 and R01NS33123 awarded by the National Institutes of Health. The United States Government has certain rights in this invention."

And insert:
--This invention was made with government support under Grant Nos. NS033123, GM043459, GM066686, and GM065823 awarded by National Institutes of Health. The government has certain rights in the invention.--

Signed and Sealed this
Twenty-eighth Day of March, 2017

Michelle K. Lee
*Director of the United States Patent and Trademark Office*

SEQUENCE LISTING

```
<160> NUMBER OF SEQ ID NOS: 50

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
taggtgaggg cgtgcgatct gtt                                              23

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gcccgcggaa ggacgagac                                                   19

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ctcccaccca atcccgtcgg tc                                               22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
gcgatgctgc cggtaggtca tcc                                              23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ttcgcgtacg tgctcaacta cta                                              23

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tggggaagag gcttctagga g                                                21
```

```
<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gggcactgga agggtctt                                                    18

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
atggggatgt tcttgaagta ggt                                              23

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cgccaccatg atttactacg c                                                21

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tttttctccc tcacctcttc gac                                              23

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
atcttgcccc accgcgtgtt ca                                               22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
cggtcagtgg gggctgcatg ttc                                              23

<210> SEQ ID NO 13
<211> LENGTH: 23
<212> TYPE: DNA
<213> ORGANISM: Artificial Sequence
<220> FEATURE:
<223> OTHER INFORMATION: Primer
```

<400> SEQUENCE: 13
gaaatgatcc cggcggcgtt tct                                             23

<210> SEQ ID NO 14
<211> LENGTH: 20
<212> TYPE: DNA
<213> ORGANISM: PArtificial Sequence
<220> FEATURE:
<223> OTHER INFORMATION: Primer

<400> SEQUENCE: 14
ggcagcaagg cgggatggtg                                                 20

<210> SEQ ID NO 15
<211> LENGTH: 511
<212> TYPE: PRT
<213> ORGANISM: HOMO SAPIENS

<400> SEQUENCE: 15

```
Met Gly Gln Gly Asp Glu Ser Glu Arg Ile Val Ile Asn Val Gly Gly
 1               5                  10                  15

Thr Arg His Gln Thr Tyr Arg Ser Thr Leu Arg Thr Leu Pro Gly Thr
             20                  25                  30

Arg Leu Ala Trp Leu Ala Glu Pro Asp Ala His Ser His Phe Asp Tyr
         35                  40                  45

Asp Pro Arg Ala Asp Glu Phe Phe Phe Asp Arg His Pro Gly Val Phe
     50                  55                  60

Ala His Ile Leu Asn Tyr Tyr Arg Thr Gly Lys Leu His Cys Pro Ala
 65                  70                  75                  80

Asp Val Cys Gly Pro Leu Tyr Glu Glu Glu Leu Ala Phe Trp Gly Ile
                 85                  90                  95

Asp Glu Thr Asp Val Glu Pro Cys Cys Trp Met Thr Tyr Arg Gln His
            100                 105                 110

Arg Asp Ala Glu Glu Ala Leu Asp Ser Phe Gly Gly Ala Pro Leu Asp
        115                 120                 125

Asn Ser Ala Asp Asp Ala Asp Ala Asp Gly Pro Gly Asp Ser Gly Asp
    130                 135                 140

Gly Glu Asp Glu Leu Glu Met Thr Lys Arg Leu Ala Leu Ser Asp Ser
145                 150                 155                 160

Pro Asp Gly Arg Pro Gly Gly Phe Trp Arg Arg Trp Gln Pro Arg Ile
                165                 170                 175

Trp Ala Leu Phe Glu Asp Pro Tyr Ser Ser Arg Tyr Ala Arg Tyr Val
            180                 185                 190

Ala Phe Ala Ser Leu Phe Phe Ile Leu Val Ser Ile Thr Thr Phe Cys
        195                 200                 205

Leu Glu Thr His Glu Arg Phe Asn Pro Ile Val Asn Lys Thr Glu Ile
    210                 215                 220

Glu Asn Val Arg Asn Gly Thr Gln Val Arg Tyr Tyr Arg Glu Ala Glu
225                 230                 235                 240

Thr Glu Ala Phe Leu Thr Tyr Ile Glu Gly Val Cys Val Val Trp Phe
                245                 250                 255

Thr Phe Glu Phe Leu Met Arg Val Ile Phe Cys Pro Asn Lys Val Glu
            260                 265                 270

Phe Ile Lys Asn Ser Leu Asn Ile Ile Asp Phe Val Ala Ile Leu Pro
        275                 280                 285

Phe Tyr Leu Glu Val Gly Leu Ser Gly Leu Ser Ser Lys Ala Ala Lys
    290                 295                 300
```

Asp Val Leu Gly Phe Leu Arg Val Arg Phe Val Arg Ile Leu Arg
305                 310                 315                 320

Ile Phe Lys Leu Thr Arg His Phe Val Gly Leu Arg Val Leu Gly His
                325                 330                 335

Thr Leu Arg Ala Ser Thr Asn Glu Phe Leu Leu Ile Ile Phe Leu
            340                 345                 350

Ala Leu Gly Val Leu Ile Phe Ala Thr Met Ile Tyr Tyr Ala Glu Arg
        355                 360                 365

Ile Gly Ala Gln Pro Asn Asp Pro Ser Ala Ser Glu His Thr His Phe
370                 375                 380

Lys Asn Ile Pro Ile Gly Phe Trp Trp Ala Val Val Thr Met Thr Thr
385                 390                 395                 400

Leu Gly Tyr Gly Asp Met Tyr Pro Gln Thr Trp Ser Gly Met Leu Val
                405                 410                 415

Gly Ala Leu Cys Ala Leu Ala Gly Val Leu Thr Ile Ala Met Pro Val
            420                 425                 430

Pro Val Ile Val Asn Asn Phe Gly Met Tyr Tyr Ser Leu Ala Met Ala
        435                 440                 445

Lys Gln Lys Leu Pro Lys Lys Lys Lys His Ile Pro Arg Pro Pro
450                 455                 460

Gln Leu Gly Ser Pro Asn Tyr Cys Lys Ser Val Val Asn Ser Pro His
465                 470                 475                 480

His Ser Thr Gln Ser Asp Thr Cys Pro Leu Ala Gln Glu Glu Ile Leu
                485                 490                 495

Glu Ile Asn Arg Ala Gly Arg Lys Pro Leu Arg Gly Met Ser Ile
            500                 505                 510

<210> SEQ ID NO 16
<211> LENGTH: 638
<212> TYPE: PRT
<213> ORGANISM: HOMO SAPIENS

<400> SEQUENCE: 16

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Pro Gly Asp Cys Leu Thr
        35                  40                  45

Thr Ala Gly Asp Lys Leu Gln Pro Ser Pro Pro Leu Ser Pro Pro
    50                  55                  60

Pro Arg Ala Pro Pro Leu Ser Pro Gly Pro Gly Cys Phe Glu Gly
65                  70                  75                  80

Gly Ala Gly Asn Cys Ser Ser Arg Gly Arg Ala Ser Asp His Pro
                85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
        115                 120                 125

Val Cys Gly Pro Leu Phe Glu Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

```
Gly Asp Pro Gly Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
    290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
        435                 440                 445

Ser Gly Met Leu Val Gly Ala Leu Cys Ala Leu Ala Gly Val Leu Thr
450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525

Asp Asn Arg Leu Leu Glu His Asn Arg Ser Val Leu Ser Gly Asp Asp
530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
            580                 585                 590

Lys Gly Tyr Glu Lys Ser Arg Ser Leu Asn Asn Ile Ala Gly Leu Ala
        595                 600                 605
```

-continued

```
Gly Asn Ala Leu Arg Leu Ser Pro Val Thr Ser Pro Tyr Asn Ser Pro
    610                 615                 620

Cys Pro Leu Arg Arg Ser Arg Ser Pro Ile Pro Ser Ile Leu
625                 630                 635
```

<210> SEQ ID NO 17
<211> LENGTH: 757
<212> TYPE: PRT
<213> ORGANISM: HOMO SAPIENS

<400> SEQUENCE: 17

```
Met Leu Ser Ser Val Cys Val Ser Ser Phe Arg Gly Arg Gln Gly Ala
 1               5                  10                  15

Ser Lys Gln Gln Pro Ala Pro Pro Gln Pro Pro Glu Ser Pro Pro
            20                  25                  30

Pro Pro Pro Leu Pro Pro Gln Gln Gln Gln Pro Ala Gln Pro Gly Pro
        35                  40                  45

Ala Ala Ser Pro Ala Gly Pro Pro Ala Pro Arg Gly Pro Gly Asp Arg
    50                  55                  60

Arg Ala Glu Pro Cys Pro Gly Leu Pro Ala Ala Ala Met Gly Arg His
65                  70                  75                  80

Gly Gly Gly Gly Gly Asp Ser Gly Lys Ile Val Ile Asn Val Gly Gly
                85                  90                  95

Val Arg His Glu Thr Tyr Arg Ser Thr Leu Arg Thr Leu Pro Gly Thr
            100                 105                 110

Arg Leu Ala Gly Leu Thr Glu Pro Glu Ala Ala Ala Arg Phe Asp Tyr
        115                 120                 125

Asp Pro Gly Ala Asp Glu Phe Phe Phe Asp Arg His Pro Gly Val Phe
    130                 135                 140

Ala Tyr Val Leu Asn Tyr Tyr Arg Thr Gly Lys Leu His Cys Pro Ala
145                 150                 155                 160

Asp Val Cys Gly Pro Leu Phe Glu Glu Glu Leu Gly Phe Trp Gly Ile
                165                 170                 175

Asp Glu Thr Asp Val Glu Ala Cys Cys Trp Met Thr Tyr Arg Gln His
            180                 185                 190

Arg Asp Ala Glu Glu Ala Leu Asp Ser Phe Glu Ala Pro Asp Pro Ala
        195                 200                 205

Gly Ala Ala Asn Ala Ala Asn Ala Ala Gly Ala His Asp Gly Gly Leu
    210                 215                 220

Asp Asp Glu Ala Gly Ala Gly Gly Gly Leu Asp Gly Ala Gly Gly
225                 230                 235                 240

Glu Leu Lys Arg Leu Cys Phe Gln Asp Ala Gly Gly Ala Gly Gly
                245                 250                 255

Pro Pro Gly Gly Ala Gly Gly Ala Gly Gly Thr Trp Trp Arg Arg Trp
            260                 265                 270

Gln Pro Arg Val Trp Ala Leu Phe Glu Asp Pro Tyr Ser Ser Arg Ala
        275                 280                 285

Ala Arg Tyr Val Ala Phe Ala Ser Leu Phe Phe Ile Leu Ile Ser Ile
    290                 295                 300

Thr Thr Phe Cys Leu Glu Thr His Glu Gly Phe Ile His Ile Ser Asn
305                 310                 315                 320

Lys Thr Val Thr Gln Ala Ser Pro Ile Pro Gly Ala Pro Pro Glu Asn
                325                 330                 335

Ile Thr Asn Val Glu Val Glu Thr Glu Pro Phe Leu Thr Tyr Val Glu
            340                 345                 350
```

```
Gly Val Cys Val Val Trp Phe Thr Phe Glu Phe Leu Met Arg Ile Thr
            355                 360                 365

Phe Cys Pro Asp Lys Val Glu Phe Leu Lys Ser Ser Leu Asn Ile Ile
370                 375                 380

Asp Cys Val Ala Ile Leu Pro Phe Tyr Leu Glu Val Gly Leu Ser Gly
385                 390                 395                 400

Leu Ser Ser Lys Ala Ala Lys Asp Val Leu Gly Phe Leu Arg Val Val
                405                 410                 415

Arg Phe Val Arg Ile Leu Arg Ile Phe Lys Leu Thr Arg His Phe Val
                420                 425                 430

Gly Leu Arg Val Leu Gly His Thr Leu Arg Ala Ser Thr Asn Glu Phe
            435                 440                 445

Leu Leu Leu Ile Ile Phe Leu Ala Leu Gly Val Leu Ile Phe Ala Thr
        450                 455                 460

Met Ile Tyr Tyr Ala Glu Arg Ile Gly Ala Asp Pro Asp Asp Ile Leu
465                 470                 475                 480

Gly Ser Asn His Thr Tyr Phe Lys Asn Ile Pro Ile Gly Phe Trp Trp
                485                 490                 495

Ala Val Val Thr Met Thr Thr Leu Gly Tyr Gly Asp Met Tyr Pro Lys
            500                 505                 510

Thr Trp Ser Gly Met Leu Val Gly Ala Leu Cys Ala Leu Ala Gly Val
        515                 520                 525

Leu Thr Ile Ala Met Pro Val Pro Val Ile Val Asn Asn Phe Gly Met
    530                 535                 540

Tyr Tyr Ser Leu Ala Met Ala Lys Gln Lys Leu Pro Lys Lys Lys Asn
545                 550                 555                 560

Lys His Ile Pro Arg Pro Pro Gln Pro Gly Ser Pro Asn Tyr Cys Lys
                565                 570                 575

Pro Asp Pro Pro Pro Pro Pro Pro His Pro His His Gly Ser Gly
            580                 585                 590

Gly Ile Ser Pro Pro Pro Ile Thr Pro Pro Ser Met Gly Val Thr
            595                 600                 605

Val Ala Gly Ala Tyr Pro Ala Gly Pro His Thr His Pro Gly Leu Leu
    610                 615                 620

Arg Gly Gly Ala Gly Gly Leu Gly Ile Met Gly Leu Pro Pro Leu Pro
625                 630                 635                 640

Ala Pro Gly Glu Pro Cys Pro Leu Ala Gln Glu Glu Val Ile Glu Ile
                645                 650                 655

Asn Arg Ala Asp Pro Arg Pro Asn Gly Asp Pro Ala Ala Ala Ala Leu
                660                 665                 670

Ala His Glu Asp Cys Pro Ala Ile Asp Gln Pro Ala Met Ser Pro Glu
        675                 680                 685

Asp Lys Ser Pro Ile Thr Pro Gly Ser Arg Gly Arg Tyr Ser Arg Asp
    690                 695                 700

Arg Ala Cys Phe Leu Leu Thr Asp Tyr Ala Pro Ser Pro Asp Gly Ser
705                 710                 715                 720

Ile Arg Lys Ala Thr Gly Ala Pro Pro Leu Pro Pro Gln Asp Trp Arg
                725                 730                 735

Lys Pro Gly Pro Pro Ser Phe Leu Pro Asp Leu Asn Ala Asn Ala Ala
            740                 745                 750

Ala Trp Ile Ser Pro
            755
```

<210> SEQ ID NO 18
<211> LENGTH: 635
<212> TYPE: PRT
<213> ORGANISM: HOMO SAPIENS

<400> SEQUENCE: 18

```
Met Ile Ser Ser Val Cys Val Ser Ser Tyr Arg Gly Arg Lys Ser Gly
  1               5                  10                  15

Asn Lys Pro Pro Ser Lys Thr Cys Leu Lys Glu Glu Met Ala Lys Gly
             20                  25                  30

Glu Ala Ser Glu Lys Ile Ile Ile Asn Val Gly Gly Thr Arg His Glu
         35                  40                  45

Thr Tyr Arg Ser Thr Leu Arg Thr Leu Pro Gly Thr Arg Leu Ala Trp
     50                  55                  60

Leu Ala Asp Pro Asp Gly Gly Arg Pro Glu Thr Asp Gly Gly Gly
 65                  70                  75                  80

Val Gly Ser Ser Gly Ser Ser Gly Gly Gly Cys Glu Phe Phe Phe
                 85                  90                  95

Asp Arg His Pro Gly Val Phe Ala Tyr Val Leu Asn Tyr Tyr Arg Thr
                100                 105                 110

Gly Lys Leu His Cys Pro Ala Asp Val Cys Gly Pro Leu Phe Glu Glu
            115                 120                 125

Glu Leu Thr Phe Trp Gly Ile Asp Glu Thr Asp Val Glu Pro Cys Cys
        130                 135                 140

Trp Met Thr Tyr Arg Gln His Arg Asp Ala Glu Glu Ala Leu Asp Ile
145                 150                 155                 160

Phe Glu Ser Pro Asp Gly Gly Ser Gly Ala Gly Pro Ser Asp Glu
                165                 170                 175

Ala Gly Asp Asp Glu Arg Glu Leu Ala Leu Gln Arg Leu Gly Pro His
            180                 185                 190

Glu Gly Gly Ala Gly His Gly Ala Gly Ser Gly Gly Cys Arg Gly Trp
        195                 200                 205

Gln Pro Arg Met Trp Ala Leu Phe Glu Asp Pro Tyr Ser Ser Arg Ala
    210                 215                 220

Ala Arg Val Val Ala Phe Ala Ser Leu Phe Ile Leu Val Ser Ile
225                 230                 235                 240

Thr Thr Phe Cys Leu Glu Thr His Glu Ala Phe Asn Ile Asp Arg Asn
                245                 250                 255

Val Thr Glu Ile Leu Arg Val Gly Asn Ile Thr Ser Val His Phe Arg
            260                 265                 270

Arg Glu Val Glu Thr Glu Pro Ile Leu Thr Tyr Ile Glu Gly Val Cys
        275                 280                 285

Val Leu Trp Phe Thr Leu Glu Phe Leu Val Arg Ile Val Cys Cys Pro
    290                 295                 300

Asp Thr Leu Asp Phe Val Lys Asn Leu Leu Asn Ile Ile Asp Phe Val
305                 310                 315                 320

Ala Ile Leu Pro Phe Tyr Leu Glu Val Gly Leu Ser Gly Leu Ser Ser
                325                 330                 335

Lys Ala Ala Arg Asp Val Leu Gly Phe Leu Arg Val Val Arg Phe Val
            340                 345                 350

Arg Ile Leu Arg Ile Phe Lys Leu Thr Arg His Phe Val Gly Leu Arg
        355                 360                 365

Val Leu Gly His Thr Leu Arg Ala Ser Thr Asn Glu Phe Leu Leu Leu
    370                 375                 380
```

```
Ile Ile Phe Leu Ala Leu Gly Val Leu Ile Phe Ala Thr Met Ile Tyr
385                 390                 395                 400

Tyr Ala Glu Arg Ile Gly Ala Arg Pro Ser Asp Pro Arg Gly Asn Asp
            405                 410                 415

His Thr Asp Phe Lys Asn Ile Pro Ile Gly Phe Trp Trp Ala Val Val
        420                 425                 430

Thr Met Thr Thr Leu Gly Tyr Gly Asp Met Tyr Pro Lys Thr Trp Ser
    435                 440                 445

Gly Met Leu Val Gly Ala Leu Cys Ala Leu Ala Gly Val Leu Thr Ile
450                 455                 460

Ala Met Pro Val Pro Val Ile Val Asn Asn Phe Gly Met Tyr Tyr Ser
465                 470                 475                 480

Leu Ala Met Ala Lys Gln Lys Leu Pro Lys Lys Arg Lys Lys His Val
                485                 490                 495

Pro Arg Pro Ala Gln Leu Glu Ser Pro Met Tyr Cys Lys Ser Glu Glu
            500                 505                 510

Thr Ser Pro Arg Asp Ser Thr Cys Ser Asp Thr Ser Pro Ala Arg
        515                 520                 525

Glu Glu Gly Met Ile Glu Arg Lys Arg Ala Asp Ser Lys Gln Asn Gly
530                 535                 540

Asp Ala Asn Ala Val Leu Ser Asp Glu Glu Gly Ala Gly Leu Thr Gln
545                 550                 555                 560

Pro Leu Ala Ser Ser Pro Thr Pro Glu Glu Arg Arg Ala Leu Arg Arg
                565                 570                 575

Ser Thr Thr Arg Asp Arg Asn Lys Lys Ala Ala Ala Cys Phe Leu Leu
            580                 585                 590

Ser Thr Gly Asp Tyr Ala Cys Ala Asp Gly Ser Val Arg Lys Gly Thr
        595                 600                 605

Phe Val Leu Arg Asp Leu Pro Leu Gln His Ser Pro Glu Ala Ala Cys
    610                 615                 620

Pro Pro Thr Ala Gly Thr Leu Phe Leu Pro His
625                 630                 635

<210> SEQ ID NO 19
<211> LENGTH: 3176
<212> TYPE: DNA
<213> ORGANISM: HOMO SAPIENS

<400> SEQUENCE: 19
accggtcccg cctcccttga cgccccgccc cgcccctcct ccctgctctc ttagaaagag      60
ccaatcgctc cgtctcattg gcggccccga ctcgtccagc tgggtcgcgt tagagtgccc     120
gccccactcc tccagccac agcccgccc cacctccccc aggccaatca gtttggttcc     180
tctcccctaa gccacgcccc cgctacctcg ctcctcctcc acccaatcc cgtcggtctc     240 tccccccgtg tccccgcccc tgcgtccccg ccctcccgc ccgccccccc gtccaatgct     300
gagctcagtc tgcgtctcgt ccttccgcgg gcgccagggg gccagcaagc agcagccggc     360
gccaccgccg cagccgcccg agtccccgcc gccgccaccg ctgccgccgc agcagcagca     420
gcctgcgcag cccggccccg ccgcgtcccc ggcgggcccc ccggcacccc gcgggccgg     480 ggaccggcgc gccgagccat gccccgggct gccggcggcg ccatggggc ggcacggcgg     540 cggcggtggc gacagcggca agatcgtgat caacgtgggc ggcgtgcgcc atgagacgta     600
ccgctcgacg ctgcgcaccc tgccggggac gcggctggcc ggcctgacgg agcccgaggc     660
ggcggcacgc ttcgactacg acccgggcgc cgacgagttc ttctttgacc ggcacccggg     720
```

-continued

```
agtcttcgcg tacgtgctca actactaccg caccggcaag ctgcactgcc cagccgacgt    780
gtgcgggccc ctgtttgagg aggagctcgg cttctgggc  atcgacgaga ccgacgtgga    840
ggcctgctgc tggatgacct accggcagca tcgcgacgct gaggaggcgc tcgactcctt    900
cgaggcgccc gaccccgcgg gcgccgccaa cgccgccaac gccgcaggcg cccacgacgg    960
aggcctggac gacgaggcgg gcgcgggcgg cggcggcctg gacggagcgg gcggcgagct   1020
caagcgcctc tgcttccagg acgcgggcgg cggcgccggg gggccgccag ggggcgcggg   1080
cggcgcgggc ggcacatggt ggcgccgctg gcagccccgc gtgtgggcgc tcttcgagga   1140
cccctactcg tcgcgggctg ccaggtatgt ggccttcgcc tccctcttct tcatcctcat   1200
ctccatcacc accttctgcc tggaaaccca tgagggcttc atccatatta gcaacaagac   1260
ggtgacccag gcctccccga tccccggggc acctccggag aacatcacca acttggaggt   1320
ggagacggag cccttcctga cctacgtgga gggggtgtgc gtggtctggt tcaccttcga   1380
gttcctcatg cgcatcacct tctgcccaga caaggtggga tttcttaaaa gcagcctcaa   1440
catcatcgac tgtgtggcca tcctgccctt ctatctcgag gtgggcctct cgggcctcag   1500
ctccaaggcc gccaaagacg tgctgggctt cctgcgggtg gtccgcttcg tccgcatcct   1560
gcgcatcttc aagctgaccc ggcacttcgt ggggctgcgc gtgctgggac acacgctccg   1620
cgccagcacc aacgagttcc tgctgctcat catcttcctg gccctggggg tgctcatctt   1680
cgccaccatg atttactacg ctgagcgcat ggcgccgac  cccgatgaca tcctgggctc   1740
caaccacacc tacttcaaga acatccccat tggcttctgg tgggctgtgg tcaccatgac   1800
gaccctgggc tatggagaca tgtaccccaa cgtggtcg   gggatgctgg tcggggcgct   1860
gtgtgccctg gcgggggtgc tgaccatcgc catgcctgtg cccgtcattg tcaacaactt   1920
tggcatgtac tattcgctgg ccatggccaa gcagaagctg cccaagaaga gaacaaaca   1980
catccccgg  ccccgcaac  cgggctcgcc caactactgc aagcctgacc cacccccgcc   2040
accccgccc  cacccgcacc acggcagcgg gggcatcagc ccgccgccac ccatcacccc   2100
accctccatg ggggtgactg tggccggggc ctacccagcg gggcccacac cgcacccgg    2160
gctgctcagg gggggagcgg gtgggctggg gatcatgggg ctgcctcctc tgccagcccc   2220
cggcgagcct tgcccgttgg ctcaggagga ggtgattgag atcaaccggg cagatcctcg   2280
ccccaatggg gatccggcag cagctgcgct tgcccacgag gactgccag ccattgacca    2340
gcctgccatg tccccggaag acaagagccc catcacgcct ggaagccgtg ccgctatag    2400
ccgggaccga gcctgcttcc tcctcaccga ctatgcccct ccccctgatg ctccatccg    2460
aaaagccact ggtgctcccc cactgccccc ccaagactgg cgtaagccag gccccccaag   2520
cttcttgccc gacctcaacg ccaacgccgc ggcctggata tcccctagt  ggacgaaccc    2580
cctccccccg ggctcttgtc accgcctgag acctcgcgag actttcggtc ccccccgccc   2640
cttcccccca ggttagcaat tgggaatggc tgggagggg  tgtccccaag acactgggct   2700
tcaaatctcc ccccaagccc tccctcctac gatcaagaca cctttgtcc  agacagctcc   2760
cttagcgttg cctggaaaag ccacagagct cctgcgggg  gtgcagaacc ctgcaggcag    2820
ccccaggctt tgcagaaacc acacacactg ttgctggatc ttgagtccca ttagctgtga   2880
gatgcctgtg agagccttcc cgcacccgtc agaagctcag agccttcttg gaccctttaa   2940
agatgtccct ctccccagcc ctccgcctca ccgcccccca ccccgaccc  cgtccttaga    3000
atcttctgga ggagcctccc tcccccccca ccccccccca ctgctcctgg agttctcatc   3060
```

```
ggattccccca agggcactgc cagcttcgct ccactcagcc cccttgcaga ccccaccccc    3120
tgcctgctct ctttccctac aactaggtca gcccccagcc ccgctacggc ggccgc         3176
```

<210> SEQ ID NO 20
<211> LENGTH: 23
<212> TYPE: PRT
<213> ORGANISM: HOMO SAPIENS

<400> SEQUENCE: 20

Phe Leu Arg Val Val Arg Phe Val Arg Ile Leu Arg Ile Phe Lys Leu
 1               5                   10                  15

Thr Arg His Phe Val Gly Leu
            20

<210> SEQ ID NO 21
<211> LENGTH: 22
<212> TYPE: PRT
<213> ORGANISM: HOMO SAPIENS

<400> SEQUENCE: 21

Phe Leu Leu Leu Ile Ile Phe Leu Ala Leu Gly Val Leu Ile Phe Ala
 1               5                   10                  15

Thr Met Ile Tyr Tyr Ala
            20

<210> SEQ ID NO 22
<211> LENGTH: 69
<212> TYPE: DNA
<213> ORGANISM: HOMO SAPIENS

<400> SEQUENCE: 22

```
ttcctgcggg tggtccgctt cgtccgcatc ctgcgcatct tcaagctgac ccggcacttc    60
gtggggctg                                                            69
```

<210> SEQ ID NO 23
<211> LENGTH: 66
<212> TYPE: DNA
<213> ORGANISM: HOMO SAPIENS

<400> SEQUENCE: 23

```
ttcctgctgc tcatcatctt cctggccctg ggggtgctca tcttcgccac catgatttac    60
tacgct                                                               66
```

<210> SEQ ID NO 24
<211> LENGTH: 23
<212> TYPE: PRT
<213> ORGANISM: Tetraodon nigroviridis

<400> SEQUENCE: 24

Phe Leu Arg Val Val Arg Phe Val Arg Ile Leu Arg Ile Phe Lys Leu
 1               5                   10                  15

Thr Arg His Phe Val Gly Leu
            20

<210> SEQ ID NO 25
<211> LENGTH: 22
<212> TYPE: PRT
<213> ORGANISM: Tetraodon nigroviridis

```
<400> SEQUENCE: 25

Phe Leu Leu Leu Ile Ile Phe Leu Ala Leu Gly Val Leu Ile Phe Ala
1               5                   10                  15

Thr Met Ile Tyr Tyr Ala
            20

<210> SEQ ID NO 26
<211> LENGTH: 23
<212> TYPE: PRT
<213> ORGANISM: Fugu rubripes

<400> SEQUENCE: 26

Phe Leu Arg Val Val Arg Phe Val Arg Ile Leu Arg Ile Phe Lys Leu
1               5                   10                  15

Thr Arg His Phe Val Gly Leu
            20

<210> SEQ ID NO 27
<211> LENGTH: 22
<212> TYPE: PRT
<213> ORGANISM: Fugu rubripes

<400> SEQUENCE: 27

Phe Leu Leu Leu Ile Ile Phe Leu Ala Leu Gly Val Leu Ile Phe Ala
1               5                   10                  15

Thr Met Ile Tyr Tyr Ala
            20

<210> SEQ ID NO 28
<211> LENGTH: 23
<212> TYPE: PRT
<213> ORGANISM: Mus musculus

<400> SEQUENCE: 28

Phe Leu Arg Val Val Arg Phe Val Arg Ile Leu Arg Ile Phe Lys Leu
1               5                   10                  15

Thr Arg His Phe Val Gly Leu
            20

<210> SEQ ID NO 29
<211> LENGTH: 22
<212> TYPE: PRT
<213> ORGANISM: Mus musculus

<400> SEQUENCE: 29

Phe Leu Leu Leu Ile Ile Phe Leu Ala Leu Gly Val Leu Ile Phe Ala
1               5                   10                  15

Thr Met Ile Tyr Tyr Ala
            20

<210> SEQ ID NO 30
<211> LENGTH: 23
<212> TYPE: PRT
<213> ORGANISM: Rattus norvegicus

<400> SEQUENCE: 30

Phe Leu Arg Val Val Arg Phe Val Arg Ile Leu Arg Ile Phe Lys Leu
1               5                   10                  15

Thr Arg His Phe Val Gly Leu
            20
```

```
<210> SEQ ID NO 31
<211> LENGTH: 22
<212> TYPE: PRT
<213> ORGANISM: Rattus norvegicus

<400> SEQUENCE: 31
```

Phe Leu Leu Leu Ile Ile Phe Leu Ala Leu Gly Val Leu Ile Phe Ala
 1               5                  10                  15

Thr Met Ile Tyr Tyr Ala
            20

```
<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
ctggaagggt cttctggatg tta                                       23

<210> SEQ ID NO 33
<211> LENGTH: 13
<212> TYPE: DNA
<213> ORGANISM: Human

<400> SEQUENCE: 33
ggtctcyctc tat                                                  13

<210> SEQ ID NO 34
<211> LENGTH: 13
<212> TYPE: DNA
<213> ORGANISM: Human

<400> SEQUENCE: 34
tcccctyctc cct                                                  13

<210> SEQ ID NO 35
<211> LENGTH: 13
<212> TYPE: DNA
<213> ORGANISM: Human

<400> SEQUENCE: 35 cgtctttkaaa tag                                                 13

<210> SEQ ID NO 36
<211> LENGTH: 13
<212> TYPE: DNA
<213> ORGANISM: Human

<400> SEQUENCE: 36
agtctgygtc tcg                                                  13

<210> SEQ ID NO 37
<211> LENGTH: 15
<212> TYPE: DNA
<213> ORGANISM: Human

<400> SEQUENCE: 37
aacgccgcca acgcc                                                15

<210> SEQ ID NO 38
<211> LENGTH: 13
<212> TYPE: DNA
<213> ORGANISM: Human
```

-continued

```
<400> SEQUENCE: 38
caccaaygag ttc                                                              13

<210> SEQ ID NO 39
<211> LENGTH: 13
<212> TYPE: DNA
<213> ORGANISM: Human

<400> SEQUENCE: 39
tcatgcrcat cac                                                              13

<210> SEQ ID NO 40
<211> LENGTH: 13
<212> TYPE: DNA
<213> ORGANISM: Human

<400> SEQUENCE: 40
tcgtccrcat cct                                                              13

<210> SEQ ID NO 41
<211> LENGTH: 13
<212> TYPE: DNA
<213> ORGANISM: Human

<400> SEQUENCE: 41
tcctgcrcat ctt                                                              13

<210> SEQ ID NO 42
<211> LENGTH: 13
<212> TYPE: DNA
<213> ORGANISM: Human

<400> SEQUENCE: 42
ctacgtrgag ggg                                                              13

<210> SEQ ID NO 43
<211> LENGTH: 13
<212> TYPE: DNA
<213> ORGANISM: Human

<400> SEQUENCE: 43
gcccccmcta ctg                                                              13

<210> SEQ ID NO 44
<211> LENGTH: 13
<212> TYPE: DNA
<213> ORGANISM: Human

<400> SEQUENCE: 44
aggagarggg gat                                                              13

<210> SEQ ID NO 45
<211> LENGTH: 13
<212> TYPE: DNA
<213> ORGANISM: Human

<400> SEQUENCE: 45
agagggrgat ggg                                                              13

<210> SEQ ID NO 46
<211> LENGTH: 13
<212> TYPE: DNA
<213> ORGANISM: Human
```

-continued

```
<400> SEQUENCE: 46
cccaacyctc tgg                                                         13

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
ttttctccct cacctcttcg ac                                               22

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
gcccgcgaaa ggacgagac                                                   19

<210> SEQ ID NO 49
<211> LENGTH: 20
<212> TYPE: PRT
<213> ORGANISM: Human

<400> SEQUENCE: 49

Val Glu Gly Val Cys Val Val Trp Phe Thr Phe Glu Phe Leu Met Arg
 1               5                  10                  15

Ile Thr Phe Cys
            20

<210> SEQ ID NO 50
<211> LENGTH: 60
<212> TYPE: DNA
<213> ORGANISM: Human

<400> SEQUENCE: 50
gtggaggggg tgtgcgtggt ctggttcacc ttcgagttcc tcatgcgcat caccttctgc     60
```